United States Patent
Dai et al.

(10) Patent No.: US 12,173,008 B2
(45) Date of Patent: *Dec. 24, 2024

(54) SUBSTITUTED PIPERAZINES AS BTK INHIBITORS

(71) Applicant: HUTCHISON MEDIPHARMA LIMITED, Shanghai (CN)

(72) Inventors: Guangxiu Dai, Shanghai (CN); Kun Xiao, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,762

(22) Filed: Apr. 17, 2023

(65) Prior Publication Data
US 2023/0382916 A1     Nov. 30, 2023

Related U.S. Application Data

(63) Continuation of application No. 17/728,097, filed on Apr. 25, 2022, now Pat. No. 11,655,254, which is a continuation of application No. PCT/CN2021/119056, filed on Sep. 17, 2021.

(30) Foreign Application Priority Data

Sep. 21, 2020  (CN) .................. 202010993583.8
Feb. 7, 2021   (CN) .................. 202110175357.3
Sep. 15, 2021  (CN) .................. 202111077860.1

(51) Int. Cl.
| | | |
|---|---|---|
| A61K 31/496 | (2006.01) | |
| A61K 45/06  | (2006.01) | |
| A61P 19/02  | (2006.01) | |
| C07D 241/04 | (2006.01) | |
| C07D 487/04 | (2006.01) | |

(52) U.S. Cl.
CPC ............ *C07D 487/04* (2013.01); *A61K 45/06* (2013.01); *A61P 19/02* (2018.01)

(58) Field of Classification Search
CPC ......................... A61K 31/496; C07D 241/04
USPC .................................... 514/252.13; 544/359
See application file for complete search history.

(56) References Cited

U.S. PATENT DOCUMENTS

| 11,478,474 B2   | 10/2022 | Dai et al. |
| 2018/0194762 A1 | 7/2018  | Atallah et al. |
| 2023/0043030 A1 | 2/2023  | Dai et al. |

FOREIGN PATENT DOCUMENTS

| CN | 110256446 A       | 9/2019  |
| WO | WO 2010/006947 A1 | 1/2010  |
| WO | WO 2011/140488 A1 | 11/2011 |
| WO | WO 2013/067260 A1 | 5/2013  |
| WO | WO 2013/067264 A1 | 5/2013  |
| WO | WO 2013/067274 A1 | 5/2013  |
| WO | WO 2013/067277 A1 | 5/2013  |
| WO | WO 2013/083666 A1 | 6/2013  |
| WO | WO 2015/000949 A1 | 1/2015  |
| WO | WO 2015/082583 A1 | 6/2015  |
| WO | WO 2016/050921 A1 | 4/2016  |
| WO | WO 2016/057500 A1 | 4/2016  |
| WO | WO 2018/035080 A1 | 2/2018  |
| WO | WO 2018/109050 A1 | 6/2018  |
| WO | WO 2019/161152 A1 | 8/2019  |
| WO | WO 2020/176403 A1 | 9/2020  |
| WO | WO 2021/164735 A1 | 8/2021  |
| WO | WO 2022/057894 A1 | 3/2022  |

OTHER PUBLICATIONS

Crawford et al., "Discovery of GDC-0853: A Potent, Selective, and Noncovalent Bruton's Tyrosine Kinase Inhibitor in Early Clinical Development," *J. Med. Chem.*, (2018), 61, 2227-2245.
Jordan, V. C., "Tamoxifen: A Most Unlikely Pioneering Medicine", *Nature Reviews: Drug Discovery*, vol. 2, pp. 205-213, (2003).
Hackam, et al., "Translation of Research Evidence From Animals to Humans", *JAMA*, 296(14), pp. 1731-1732, (2006).
Vippagunta, et al., "Crystalline Solids", *Advanced Drug Delivery Reviews*, vol. 48, pp. 3-26, (2001).

*Primary Examiner* — Douglas M Willis
(74) *Attorney, Agent, or Firm* — Hoxie & Associates LLC

(57) ABSTRACT

The present invention relates to heteroaryl heterocyclic compounds of formula (I), pharmaceutical compositions comprising same, methods for preparing same, and uses thereof, wherein the variables are as defined in the description.

34 Claims, 2 Drawing Sheets

SUBSTITUTED PIPERAZINES AS BTK INHIBITORS

CROSS-REFERENCE TO RELATED APPLICATIONS

This application is a continuation application of U.S. application Ser. No. 17/728,097, filed on Apr. 25, 2022, which is a continuation of International Application No. PCT/CN2021/119056, filed on Sep. 17, 2021, which claims the priority benefits of CN Application No. 202010993583.8, filed on Sep. 21, 2020, CN Application No. 202110175357.3, filed on Feb. 7, 2021, and CN Application No. 202111077860.1, filed on Sep. 15, 2021; the contents of which are herein incorporated by reference in their entirety.

FIELD OF THE INVENTION

The present invention relates to heteroaryl heterocyclic compounds, pharmaceutical compositions comprising same, methods for preparing same, and uses thereof.

BACKGROUND OF THE INVENTION

Bruton's Tyrosine kinase (BTK), a member of non-receptor tyrosine protein Tec family (including BTK, LTK, TEC, BMX, TXK and the like), is widely expressed in hematopoietic cells except for T cells, NK cells and differentiated plasma cells. BTK plays an important role in signaling mediated by B cell antigen receptor (BCR) and Fcγ receptor (FcγR) in B cells and myeloid cells, respectively. It is a key regulator on the B cell development, activation, signaling and survival. BTK can control the development and differentiation of B cells by activating positive regulatory factors and differentiation factors of cell cycle, and can also control the survival and proliferation of B cells by regulating the expressions of pro-apoptotic proteins and anti-apoptotic proteins. BTK also plays an important role in the migration and adhesion of B lymphoma cells. In addition, BTK plays a role in many other hematopoietic signaling pathways, such as Toll-like receptor (TLR) and cytokine receptor-mediated TNF-α production in macrophages, signaling mediated by IgE receptor (FceRI) in mast cells, inhibition of Fas/APO-1 induced apoptotic signal in B-type lymphoid cells, and collagen induced platelet aggregation.

In humans, BTK gene mutation would lead to a hereditary immunodeficiency disease, X-linked agammaglobulinaemia (XLA). Point mutation of BTK gene is implicated in human XLA patients, associated with low to undetectable BTK mRNA level and BTK protein expression, as a consequence, almost completely lack of the maturation and the development of B cells and immunoglobulins, and significant attenuation of persistent calcium signal in response to BCR stimulation. The effect of BTK mutation is only restricted on B cell populations, no significant development defects in other immune cells found in XLA patients. Spontaneous mutations of BTK gene were also found in X-linked immunodeficiency (xid) mice, showing a similar but less severe phenotype. In xid mice or mutation induced BTK gene knock-out mice, B cell differentiation was partially blocked at the B cell stage, with reduced number of mature B cells in blood circulation, and resistance to models of collagen-induced arthritis and *staphylococcus*-induced arthritis. It has been indicated by a large amount of evidence that BTK is abundantly expressed in the circulating B cells in the patients with autoimmune diseases such as rheumatoid arthritis (RA), primary Sjogren's syndrome (pSS) and systemic lupus erythematosus (SLE), as well as B-cell leukemia and lymphoma. The aberrant activation of BCR signaling has been confirmed in these autoimmune diseases and B cell related diseases. Inhibition of B cells, BCR signaling pathway and BTK may slow down the progression of the diseases to varying degrees.

Based on the key role of BTK in the development and functions of B cells, BTK is considered as a potential target for the treatment of B cell malignancies and autoimmune diseases. A variety of BTK inhibitors are being developed for the clinical research of hematologic malignancies and autoimmune diseases. Small molecule BTK inhibitors (such as ibrutinib, acalabrutinib, zanubrutinib, PRN1008, GDC-0853) have shown promising therapeutic efficacies. For example, ibrutinib, an irreversible BTK inhibitor, with a relatively high durable efficacy and low toxicity in clinical studies, has been approved by U.S. Food and Drug Administration (FDA) for the treatment of relapsed mantle cell lymphoma (MCL) in 2013, chronic lymphocytic leukemia (CLL) in 2014, Waldenstrom's macroglobulinaemia (WM) in 2015, and relapsed/refractory marginal zone lymphoma (MZL) in 2017. In particular, the approved indications were extended to chronic graft-versus-host disease (GVHD) in 2017, demonstrating the mechanism of BTK in the treatment of chronic autoimmune diseases. In addition, the irreversible BTK inhibitor acalabrutinib was approved for the treatment of adult MCL in 2017 and for CLL in 2019; zanubrutinib was approved by FDA for the treatment of MCL in November 2019; and a phase 3 study of PRN1008 against pemphigus is ongoing. Some irreversible BTK inhibitors (tirabrutinib, spebrutinib, and evobrutinib) and reversible BTK inhibitors (GDC-0853, ARQ-531 and LOXO-305) have been on the stage of pre-clinical and clinical development.

Therefore, BTK inhibitors represent attractive therapy for the treatment of related diseases, especially autoimmune diseases, inflammatory diseases or cancer.

SUMMARY OF THE INVENTION

Provided is a compound of formula (I):

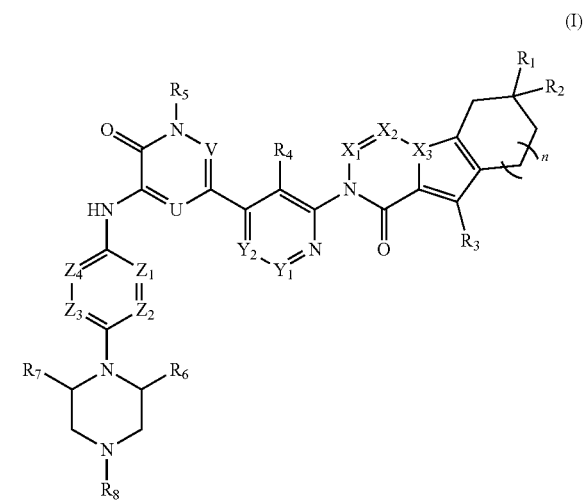

or a pharmaceutically acceptable salt thereof, or a solvate, a racemic mixture, an enantiomer, a diastereomer or a tautomer thereof, wherein $X_1$, $X_2$ and $X_3$ are each independently CH or N;

U and V are each independently N or $CR_9$;

$Y_1$ and $Y_2$ are each independently $CR_{10}$ or N;

$R_1$ and $R_2$ are each independently chosen from hydrogen, deuterium, halogen, —CN, hydroxyl, $C_{1-6}$ alkyl, $C_{3-6}$ cycloalkyl, $C_{2-6}$ alkynyl, $C_{1-6}$ deuteroalkyl and $C_{1-6}$ haloalkyl; or $R_1$ and $R_2$ together with the carbon atom to which they are attached form 3-6 membered cycloalkyl;

$R_3$ is hydrogen, deuterium, halogen, —CN or $C_{1-6}$ haloalkyl;

$R_4$ is hydrogen, halogen, —CN, $C_{1-6}$ alkyl, $C_{2-6}$ alkynyl, —($C_{1-3}$ alkyl)-OH, —($C_{1-3}$ alkyl)-O—($C_{1-3}$ alkyl), —O—($C_{1-3}$ alkyl), —CHO, —C(O)NH$_2$, —C(O)NHCH$_3$, —C(O)N(CH$_3$)$_2$ or 3-hydroxyloxetan-3-yl, wherein the $C_{1-6}$ alkyl or $C_{1-3}$ alkyl is each optionally substituted with one or more deuterium or halogen;

$R_5$ is chosen from hydrogen, $C_{1-6}$ alkyl and $C_{3-6}$ cycloalkyl, wherein the $C_{1-6}$ alkyl is optionally substituted with one or more deuterium or halogen;

$Z_1$, $Z_2$, $Z_3$ and $Z_4$ are each independently CH or N, provided that at least one of $Z_1$, $Z_2$, $Z_3$ and $Z_4$ is N;

$R_6$ and $R_7$ are each independently chosen from $C_{1-6}$ alkyl;

$R_8$ is hydrogen, $C_{1-6}$ alkyl, $C_{3-6}$ cycloalkyl or 4-8 membered heterocyclyl, wherein the $C_{1-6}$ alkyl, $C_{3-6}$ cycloalkyl or 4-8 membered heterocyclyl is optionally substituted with one or more groups chosen from: deuterium, halogen, $C_{1-6}$ alkyl, trifluoromethyl, —OH, —NH$_2$, —O—($C_{1-6}$ alkyl), —NH($C_{1-6}$ alkyl) or —N($C_{1-6}$ alkyl)$_2$;

$R_9$ is hydrogen, deuterium or halogen;

$R_{10}$ is hydrogen, deuterium, halogen, CN, $C_{1-6}$ alkyl or $C_{1-6}$ haloalkyl;

n is 0, 1 or 2; provided that when n is 1, $R_3$ is not hydrogen.

The above compounds and the active compounds (including general structural formula compounds and specific compounds) disclosed in the context of the present invention, including pharmaceutically acceptable salts thereof, or solvates, racemic mixtures, enantiomers, diastereomers or tautomers thereof, which are covered by the above scope, are collectively referred to herein as "compounds of the present invention".

Also provided is a pharmaceutical composition, comprising the compounds of the present invention, and optionally comprising a pharmaceutically acceptable excipient.

Also provided is a method of in vivo or in vitro inhibiting the activity of BTK, comprising contacting BTK with an effective amount of the compounds of the present invention.

Also provided is a method of treating or preventing a disease mediated by BTK or at least in part by BTK, comprising administering to the subject in need thereof an effective amount of the compounds of the present invention.

Also provided is a method of treating or preventing an autoimmune disease, an inflammatory disease or cancer, comprising administering to the subject in need thereof an effective amount of the compounds of the present invention.

Also provided is use of the compounds of the present invention for treating or preventing a disease mediated by BTK or at least in part by BTK.

Also provided is use of the compounds of the present invention for treating or preventing an autoimmune disease, an inflammatory disease or cancer.

Also provided is use of the compounds of the present invention in the manufacture of a medicament for treating or preventing a disease mediated by BTK or at least in part by BTK.

Also provided is use of the compounds of the present invention in the manufacture of a medicament for treating or preventing an autoimmune disease, an inflammatory disease or cancer.

Also provided are the compounds of the present invention for in vivo or in vitro inhibiting the activity of BTK.

Also provided are the compounds of the present invention for use as a medicament.

Also provided is use of the compounds of the present invention for use as a medicament for treating or preventing a disease mediated by BTK or at least in part by BTK, especially for treating or preventing an autoimmune disease, an inflammatory disease or cancer.

Also provided is a pharmaceutical combination, comprising the compounds of the present invention and at least one additional therapeutic agent, wherein the therapeutic agent is preferably chosen from: an anti-inflammatory agent, an immunomodulator or an anti-tumor active agent, wherein the anti-tumor active agent includes a chemotherapeutic agent, an immune checkpoint inhibitor or agonist, and a targeted therapeutic agent.

Also provided is a kit for treating or preventing a disease mediated by BTK or at least in part by BTK. The kit can comprise the pharmaceutical composition of the present invention and instructions for use, and the pharmaceutical composition comprises the compounds of the present invention.

DETAILED DESCRIPTION OF THE INVENTION

Definitions

Figure 1:
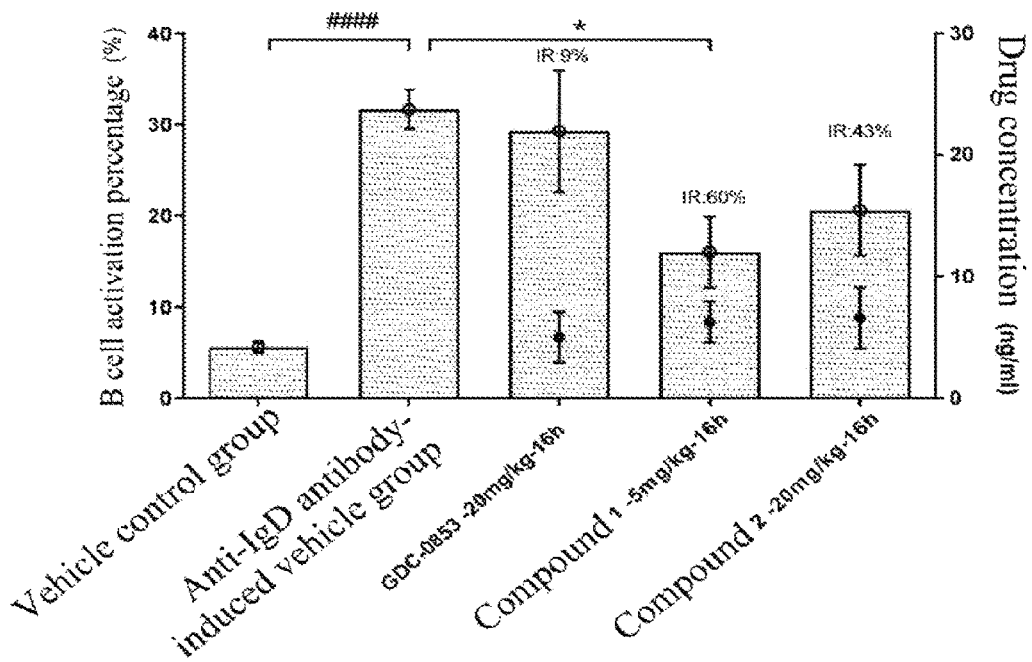
FIG. 1: Inhibiting effects of the compounds of the present invention on B cell activation in mouse whole blood induced by anti-IgD antibodies.

As used in the present application, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —OR$^3$ refers to the attachment of R$^3$ to the rest of the molecule through an oxygen atom.

The term "alkyl" as used herein refers to a straight or branched saturated hydrocarbon radical containing 1-18 carbon atoms ($C_{1-18}$), preferably 1-10 carbon atoms ($C_{1-10}$), more preferably 1-6 carbon atoms ($C_{1-6}$), and even more preferably 1-4 carbon atoms ($C_{1-4}$) or 1-3 carbon atoms ($C_{1-3}$). When the term "alkyl" is prefixed with "C", it means the number of carbon atoms. For example, "$C_{1-6}$ alkyl" refers to an alkyl containing 1-6 carbon atoms. "$C_{1-3}$ alkyl" refers to an alkyl containing 1-3 carbon atoms. Examples of $C_{1-6}$ alkyl include, but are not limited to, methyl, ethyl, propyl (e. g. n-propyl, i-propyl), butyl (e.g., n-butyl, i-butyl, s-butyl and t-butyl), pentyl (e. g. n-pentyl, i-pentyl, neopentyl), and hexyl, and the like.

The term "alkynyl" as used herein refers to a straight or branched unsaturated hydrocarbon radical containing one or more, for example 1, 2, or 3, carbon-carbon triple bonds (C≡C) and 2-18 carbon atoms ($C_{2-18}$), preferably 2-10 carbon atoms ($C_{2-10}$), more preferably 2-6 carbon atoms ($C_2$-6), and even more preferably 2-4 carbon atoms ($C_2$-4). When the term "alkynyl" is prefixed with "C", it means the number of carbon atoms. For example, "$C_{2-6}$ alkynyl" refers to an alkynyl containing 2-6 carbon atoms. "$C_{2-4}$ alkynyl" refers to an alkynyl containing 2-4 carbon atoms. Examples of $C_{2-6}$ alkynyl include, but are not limited to, ethynyl, propynyl (e.g., 2-propynyl), and butynyl (e.g., 2-butynyl), and the like. The point of attachment for the alkynyl can be on or not on the triple bonds.

The term "halogen" or "halo" as used herein means fluoro, chloro, bromo, and iodo, preferably fluoro, chloro and bromo, more preferably fluoro and chloro.

The term "haloalkyl" as used herein refers to an alkyl radical, as defined herein, in which one or more, for example 1, 2, 3, 4, or 5, hydrogen atoms are replaced with halogen atom, and when more than one hydrogen atoms are replaced with halogen atoms, the halogen atoms may be the same or different from each other. In one embodiment, the term "haloalkyl" as used herein refers to an alkyl radical, as defined herein, in which two or more, such as 2, 3, 4, or 5 hydrogen atoms are replaced with halogen atoms, wherein the halogen atoms are identical to each other. In another embodiment, the term "haloalkyl" as used herein refers to an alkyl radical, as defined herein, in which two or more hydrogen atoms, such as 2, 3, 4, or 5 hydrogen atoms are replaced with halogen atoms, wherein the halogen atoms are different from each other. When the term "haloalkyl" is prefixed with "C", it means the number of carbon atoms. For example, "$C_{1-6}$ haloalkyl" refers to a haloalkyl as defined herein containing 1-6 carbon atoms. "$C_{1-4}$ haloalkyl" refers to a haloalkyl as defined herein containing 1-4 carbon atoms. Examples of $C_{1-6}$ haloalkyl include, but are not limited to —CF$_3$, —CHF$_2$, —CH$_2$F, —CH$_2$CF$_3$, —CH(CF$_3$)$_2$, and the like.

The term "cycloalkyl" as used herein refers to saturated or partially unsaturated cyclic hydrocarbon radical having 3-12 ring carbon atoms ($C_{3-12}$), such as 3-8 ring carbon atoms ($C_{3-8}$), 5-7 ring carbon atoms ($C_{5-7}$), 4-7 ring carbon atoms ($C_4$-7) or 3-6 ring carbon atoms ($C_{3-6}$), which may have one or more rings, such as 1, 2, or 3 rings, preferably 1 or 2 rings. When the term "cycloalkyl" is prefixed with "C", it means the number of carbon atoms. For example, "$C_{3-6}$ cycloalkyl" or "3-6 membered cycloalkyl" refers to a cycloalkyl containing 3-6 ring carbon atoms. The cycloalkyl may include a fused or bridged ring, or a spirocyclic ring. The rings of the cycloalkyl may be saturated or has one or more, for example, one or two double bonds (i.e., partially unsaturated), but not fully conjugated, and not an aryl as defined herein. Examples of $C_{3-6}$ cycloalkyl include, but are not limited to cyclopropyl, cyclobutyl, cyclopentyl, cyclohexyl, spiro[2.2]pentyl, cyclopropenyl, cyclobutenyl, cyclopentenyl, cyclopentadienyl, cyclohexenyl, etc.

The term "heterocyclyl" or "heterocyclic" as used herein can be used interchangeably and each refers to saturated or partially unsaturated cyclic radicals having 3-12 ring atoms, such as 3-8 ring atoms, 4-8 ring atoms, 4-6 ring atoms or 4-5 ring atoms, and containing one or more, for example 1, 2 or 3, preferably 1 or 2 heteroatoms independently chosen from N, O and S in the rings, with the remaining ring atoms being carbon; it may have one or more rings, for example 1, 2 or 3, preferably 1 or 2 rings. The heterocyclyl also includes those wherein the N or S heteroatom are optionally oxidized to various oxidation states. The point of attachment of heterocyclyl can be on the N heteroatom or carbon. For example, "4-8 membered heterocyclyl" represents a heterocyclyl having 4-8 (4, 5, 6, 7 or 8) ring atoms comprising at least one, such as 1, 2 or 3, preferably 1 or 2 heteroatoms independently chosen from N, O and S; "4-6 membered heterocyclyl" represents a heterocyclyl having 4-6 (4, 5 or 6) ring atoms comprising at least one, preferably 1 or 2 heteroatoms independently chosen from N, O and S (preferably N and O, more preferably O), which is preferably a monocyclic ring; and "4-5 membered heterocyclyl" represents a heterocyclyl having 4 or 5 ring atoms comprising at least one, preferably 1 or 2 heteroatoms independently chosen from N, O and S (preferably N and O, more preferably O), which is a monocyclic ring. The heterocyclyl also includes a fused or bridged ring, or a spirocyclic ring. The rings of the heterocyclyl may be saturated or has one or more, for example, one or two double bonds (i.e., partially unsaturated), but not fully conjugated, and not a heteroaryl as defined herein. Examples of heterocyclyl include, but are not limited to: 4-8 membered heterocyclyl, 4-6 membered heterocyclyl, 4-5 membered heterocyclyl and 4-membered heterocyclyl, such as oxetanyl (such as oxetan-3-yl), azetidinyl, pyrrolidyl, tetrahydrofuranyl, dioxolanyl, tetrahydropyranyl, morpholinyl, thiomorpholinyl, piperidyl, piperazinyl, tetrahydropyridyl, pyrazinyl, pyrazolidinyl and oxaspiro[3.3]heptanyl, preferably oxetanyl (such as oxetan-3-yl), azetidinyl, tetrahydropyranyl, morpholinyl (such as morpholino), piperazinyl (such as piperazin-1-yl), tetrahydropyridyl (such as 1,2,3,6-tetrahydropyridyl).

The term "—OH" as used herein refers to hydroxyl radical.

The term "—CN" as used herein refers to cyano radical.

The term "oxo" as used herein refers to =O.

Any asymmetric atom (e. g. carbon, etc.) of a compound of formula (I) may exist in a racemic or enantiomeric rich form, for example in (R)-, (S) - or (RS) -configuration. In some embodiments, asymmetric atoms have at least 50%, at least 60%, at least 70%, at least 80%, at least 90%, at least 95%, at least 99%, or 100% enantiomeric excess in (R) - or (S) configurations, respectively.

The term "optional" or "optionally" as used herein means that the subsequently described event or circumstance may or may not occur, and the description includes instances wherein the event or circumstance occur and instances in which it does not occur. For example, "optionally substituted with one or more" includes unsubstituted and substituted with 1, 2, 3 or more substituents as described. It will be understood by those skilled in the art, with respect to any group containing one or more substituents, that such groups are not intended to introduce any substitution or substitution patterns that are sterically impractical, chemically incorrect, synthetically non-feasible and/or inherently unstable.

The term "substituted" or "substituted with . . . ", as used herein, means that one or more (such as, 1, 2, 3 or 4) hydrogens on the designated atom or group are replaced with one or more (such as 1, 2, 3 or 4) substituents, preferably the substituents chosen from the indicated group of substituents or radicals, provided that the designated atom's normal valence is not exceeded. Said substituents may be the same or different from each other. The term "substituted with one or more groups chosen from" or "substituted with one or more" as used herein means that one or more hydrogens on the designated atom or group are independently replaced with one or more radicals chosen from the indicated group of substituents or radicals, wherein said radicals may be the same or different from each other. Preferably, "substituted with one or more groups chosen from" or "substituted with one or more" means that the designated atom or group is substituted with 1, 2, 3, or 4 radicals independently chosen from the indicated group of substituents or radicals, wherein said radicals may be the same or different from each other. In some embodiments, when a substituent is oxo (i.e., =O), then two hydrogens on a single atom are replaced by the oxo. An optional substituent can be any radicals, provided that combinations of substituents and/or variables result in a chemically correct and stable compound. A chemically correct and stable compound is meant to imply a compound that is sufficiently robust to survive sufficient isolation from a reaction mixture to be able to identify the chemical structure of the compound. Preferably, substituents are those exemplified in the compounds of the embodiment of the present application.

Unless otherwise specified, substituents are named into the core structure. For example, it is to be understood that when (cycloalkyl)alkyl is listed as a possible substituent, the point of attachment of this substituent to the core structure is in the alkyl portion.

It will be appreciated by the person of ordinary skill in the art ("POSITA") that some of the compounds of formula (I) may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the POSITA that the present invention includes all the individual stereoisomers (e.g., enantiomers), racemic mixtures or partially resolved mixtures of the compounds of formula (I) and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (see, Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively, individual isomers can be separated chemically from a mixture by: forming diastereomeric salts with a chiral acid (such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like), fractionally crystallizing the salts, and then freeing one or both of the resolved bases, optionally repeating the process, so as obtain either or both substantially free of the other; i.e., in a form having an optical purity of >95%. Alternatively, the racemates can be covalently linked to a chiral compound (auxiliary) to produce diastereomers which can be separated by chromatography or by fractional crystallization after which time the chiral auxiliary is chemically removed to afford the pure enantiomers, as is known to the POSITA.

The term "tautomer" as used herein refers to constitutional isomers of compounds generated by rapid movement of an atom in two positions in a molecule. Tautomers readily interconvert into each other, e.g., enol form and ketone form are typical tautomers.

A "pharmaceutically acceptable salt" is intended to mean a salt of a free acid or base of a compound of Formula (I) that is non-toxic, biologically tolerable, or otherwise biologically suitable for administration to the subject. For example, an acid addition salt includes such as a salt derived from an inorganic acid and an organic acid. Said inorganic acid includes such as hydrochloric acid, hydrobromic acid, hydroiodic acid, sulfuric acid, phosphoric acid, and nitric acid; said organic acid includes such as p-toluenesulfonic acid, salicylic acid, methanesulfonic acid, oxalic acid, succinic acid, citric acid, malic acid, lactic acid, fumaric acid, and the like. For examples, see, generally, S. M. Berge, et al., "Pharmaceutical Salts", J. Pharm. Sci., 1977, 66: 1-19, and Handbook of Pharmaceutical Salts, Properties, Selection, and Use, Stahl and Wermuth, Eds., Wiley-VCH and VHCA, Zurich, 2002.

In addition, if a compound of the present invention herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. The POSITA will recognize various synthetic methodologies that may be used without undue experimentation to prepare non-toxic pharmaceutically acceptable acid addition salts or base addition salts.

The term "deuterated compound" or "deuterates" refers to a compound in which one or more hydrogen atoms, such as 1, 2, 3, 4 or 5 hydrogen atoms, are replaced by deuterium atoms (D).

The term "solvates" means solvent addition forms that contain either stoichiometric or non-stoichiometric amounts of solvent. Some compounds have a tendency to trap a fixed molar ratio of solvent molecules in the solid state, thus forming a solvate. If the solvent is water, the solvate formed is a hydrate, when the solvent is alcohol, the solvate formed is an alcoholate. Hydrates are formed by the combination of one or more molecules of water, or less than one molecule of water, with one molecule of the substances in which the water retains its molecular state as $H_2O$, such combination being able to form one or more hydrates, for example, hemihydrate, monohydrate, and dihydrate.

As used herein, the terms "group(s)" and "radical(s)" are synonymous and are intended to indicate functional groups or fragments of molecules attachable to other fragments of molecules.

The term "active ingredient" is used to indicate a chemical substance which has biological activity. In some embodiments, an "active ingredient" is a chemical substance having pharmaceutical utility.

The term "pharmaceutical combination" as used herein means a product obtained by mixing or combining two or more active ingredients, including fixed and non-fixed combinations of active ingredients, such as a kit, and a pharmaceutical composition. The term "fixed combination" means that two or more active ingredients (such as compounds of the present invention and additional therapeutic agents) are administered simultaneously to a patient in the form of a single entity or dose. The term "non-fixed combination" means that two or more active ingredients (such as compounds of the present invention and additional therapeutic agents) are administered simultaneously, in parallel or successively to a patient in separate entities, wherein the administration provides the patient with a therapeutically effective level of the compound.

The terms "treating" or "treatment" or "prevention" of a disease or disorder, in the context of achieving therapeutic benefit, refer to administering one or more pharmaceutical substances, especially a compound of formula (I) described herein to a subject that has the disease or disorder, or has a symptom of a disease or disorder, or has a predisposition toward a disease or disorder, with the purpose to cure, heal, alleviate, relieve, alter, remedy, ameliorate, improve, or affect the disease or disorder, the symptoms of the disease or disorder, or the predisposition toward the disease or disorder. In some embodiments, the disease or disorder is cancer, such as solid tumors or hematologic malignancies, including lymphoma, leukemia and myeloma. In another embodiment, the disease or disorder is an inflammatory diseases or autoimmune disease.

The terms "treating", "contacting" and "reacting," in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture and ultimately lead to the formation of the indicated and/or the desired product.

The term "effective amount" as used herein refers to an amount or dose of an BTK inhibiting agent sufficient to generally bring about a therapeutic benefit in patients in need of treatment for a disease or disorder mediated by BTK or at least in part by BTK. Effective amounts or doses of the active ingredient of the present disclosure may be ascertained by methods such as modeling, dose escalation studies or clinical trials, and by taking into consideration factors, e.g., the mode or route of administration or drug delivery, the pharmacokinetics of the agent, the severity and course of the disease or disorder, the subject's previous or ongoing therapy, the subject's health status and response to drugs, and the judgment of the attending physician.

An exemplary dose is in the range of from about 0.0001 to about 200 mg of active agent per kg of subject's body weight per day, such as from about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease or disorder has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

The term "inhibition" or "inhibiting" indicates a decrease in the baseline activity of a biological activity or process. The term "inhibition of BTK activity" is a practical pharmaceutical activity for purposes of this disclosure and refers to a decrease in the activity of BTK as a direct or indirect response to the presence of the compound of the present invention, relative to the activity of BTK in the absence of the compound of the present invention. The decrease in activity may be due to the direct interaction of the compound of the present invention with BTK, or due to the interaction of the compound of the present invention, with one or more other factors that in turn affect the BTK activity. For example, the presence of the compound of the present invention may decrease the BTK activity by directly binding to the BTK, by causing (directly or indirectly) another factor to decrease the BTK activity, or by (directly or indirectly) decreasing the amount of BTK present in the cell or organism.

The term "subject" or "patient" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" or "patient" does not denote a particular age or sex. In some embodiments, the subject or patient is a human.

In general, the term "about" is used herein to modify a numerical value above or below the stated value by a variance of 20%.

Technical and scientific terms used herein and not specifically defined have the meaning commonly understood by the POSITA to which the present disclosure pertains.

All numerical ranges herein shall be interpreted as disclosing each numerical value and subset of numerical values within the range, regardless of whether they are specifically otherwise disclosed. For example, when referring to any range of values, it should be regarded as referring to every value within the range of values, for example, every integer within the range of values. For example, $C_{1-6}$ as used herein represents the inclusion of 1, 2, 3, 4, 5 or 6 C. The invention relates to all values falling within the ranges, all smaller ranges and the upper or lower limits of the numerical range.

Detailed Description of Embodiments
Embodiment 1. A compound of formula (I):

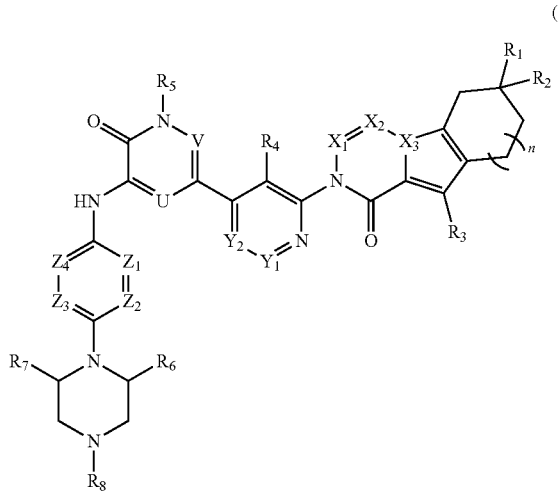

or a pharmaceutically acceptable salt thereof, or a solvate, a racemic mixture, an enantiomer, a diastereomer or a tautomer thereof, wherein
$X_1$, $X_2$ and $X_3$ are each independently CH or N;
U and V are each independently N or $CR_9$;
$Y_1$ and $Y_2$ are each independently $CR_{10}$ or N;
$R_1$ and $R_2$ are each independently chosen from hydrogen, deuterium, halogen, —CN, hydroxyl, $C_{1-6}$ alkyl, 3-6 membered cycloalkyl, $C_{2-6}$ alkynyl, $C_{1-6}$ deuteroalkyl and $C_{1-6}$ haloalkyl; or $R_1$ and $R_2$ together with the carbon atom to which they are attached form 3-6 membered cycloalkyl;
$R_3$ is hydrogen, deuterium, halogen, —CN or $C_{1-6}$ haloalkyl;
$R_4$ is hydrogen, halogen, —CN, $C_{1-6}$ alkyl, $C_{2-6}$ alkynyl, —($C_{1-3}$ alkyl)-$OH_1$, —($C_{1-3}$ alkyl)—O—($C_{1-3}$ alkyl), —O—($C_{1-3}$ alkyl), —CHO, —C(O)NH$_2$, —C(O)NHCH$_3$, —C(O)N(CH$_3$)$_2$ or 3-hydroxyl-oxetan-3-yl, wherein the $C_{1-6}$ alkyl or $C_{1-3}$ alkyl is each optionally substituted with one or more deuterium or halogen;
$R_5$ is chosen from hydrogen, $C_{1-6}$ alkyl and $C_{3-6}$ cycloalkyl, wherein the $C_{1-6}$ alkyl is optionally substituted with one or more deuterium or halogen;
$Z_1$, $Z_2$, $Z_3$ and $Z_4$ are each independently CH or N, provided that at least one of $Z_1$, $Z_2$, $Z_3$ and $Z_4$ is N;
$R_6$ and $R_7$ are each independently chosen from $C_{1-6}$ alkyl;
$R_8$ is hydrogen, $C_{1-6}$ alkyl, $C_{3-6}$ cycloalkyl or 4-8 membered heterocyclyl, wherein the $C_{1-6}$ alkyl, $C_{3-6}$ cycloalkyl or 4-8 membered heterocyclyl is optionally substituted with one or more groups chosen from: deuterium, halogen, $C_{1-6}$ alkyl, trifluoromethyl, —OH, —NH$_2$, —O—($C_{1-6}$ alkyl), —NH($C_{1-6}$ alkyl) or —N($C_{1-6}$ alkyl)$_2$;
$R_9$ is hydrogen, deuterium or halogen;
$R_{10}$ is hydrogen, deuterium, halogen, CN, $C_{1-6}$ alkyl or $C_{1-6}$ haloalkyl;
n is 0, 1 or 2; provided that when n is 1, $R_3$ is not hydrogen.
Embodiment 2. The compound or the pharmaceutically acceptable salt thereof, or the solvate, the racemic mixture, the enantiomer, the diastereomer or the tautomer thereof according to embodiment 1, wherein $R_4$ is $C_{1-6}$ alkyl, —($C_{1-3}$ alkyl)-OH, —($C_{1-3}$ deuteroalkyl)-OH, —CHO, —C(O)NH$_2$, —C(O)NHCH$_3$ or —C(O)N(CH$_3$)$_2$;
preferably, $R_4$ is $C_{1-6}$ alkyl, —($C_{1-3}$ alkyl)-OH, —($C_{1-3}$ deuteroalkyl)-OH or —CHO.
Embodiment 3. The compound or the pharmaceutically acceptable salt thereof, or the solvate, the racemic mixture, the enantiomer, the diastereomer or the tautomer thereof according to embodiment 1 or 2, wherein
$X_1$, $X_2$ and $X_3$ are each independently CH or N;
U and V are each independently $CR_9$;
$Y_1$ and $Y_2$ are each independently $CR_{10}$;
$R_1$ and $R_2$ are each independently chosen from hydrogen, deuterium, halogen, —CN, hydroxyl, $C_{1-6}$ alkyl, $C_{1-6}$ deuteroalkyl and $C_{1-6}$ haloalkyl;
$R_3$ is hydrogen, deuterium, halogen, —CN or $C_{1-6}$ haloalkyl;
$R_4$ is —($C_{1-3}$ alkyl)-OH, —C(O)NH$_2$, —C(O)NHCH$_3$ or —C(O)N(CH$_3$)$_2$, wherein the $C_{1-3}$ alkyl is optionally substituted with one or more deuterium;
$R_5$ is chosen from hydrogen and $C_{1-6}$ alkyl, wherein the $C_{1-6}$ alkyl is optionally substituted with one or more deuterium;
$Z_1$, $Z_2$, $Z_3$ and $Z_4$ are each independently CH or N, provided that at least one of $Z_1$, $Z_2$, $Z_3$ and $Z_4$ is N;
$R_6$ and $R_7$ are each independently chosen from $C_{1-6}$ alkyl;
$R_8$ is hydrogen, $C_{1-6}$ alkyl, $C_{3-6}$ cycloalkyl or 4-8 membered heterocyclyl, wherein the $C_{1-6}$ alkyl, $C_{3-6}$ cycloalkyl or 4-8 membered heterocyclyl is optionally substituted with one or more groups chosen from: deuterium, halogen, $C_{1-6}$ alkyl, trifluoromethyl, —OH or —NH$_2$;
$R_9$ is hydrogen or deuterium;
$R_{10}$ is hydrogen or deuterium;
n is 0, 1 or 2; provided that when n is 1, $R_3$ is not hydrogen.
Embodiment 4. The compound or the pharmaceutically acceptable salt thereof, or the solvate, the racemic mixture, the enantiomer, the diastereomer or the tautomer thereof according to any one of embodiments 1-3, wherein
$X_1$, $X_2$ and $X_3$ are each independently CH or N;
U and V are each independently $CR_9$;
$Y_1$ and $Y_2$ are each independently $CR_{10}$;
$R_1$ and $R_2$ are each independently chosen from hydrogen, deuterium, halogen, —CN, hydroxyl, $C_{1-6}$ alkyl, $C_{1-6}$ deuteroalkyl and $C_{1-6}$ haloalkyl;
$R_3$ is hydrogen, deuterium, halogen, —CN or $C_{1-6}$ haloalkyl;
$R_4$ is —($C_{1-3}$ alkyl)-OH, wherein the $C_{1-3}$ alkyl is optionally substituted with one or more deuterium;
$R_5$ is chosen from $C_{1-6}$ alkyl, wherein the $C_{1-6}$ alkyl is optionally substituted with one or more deuterium;
$Z_1$, $Z_2$, $Z_3$ and $Z_4$ are each independently CH or N, provided that at least one of $Z_1$, $Z_2$, $Z_3$ and $Z_4$ is N;
$R_6$ and $R_7$ are each independently chosen from $C_{1-6}$ alkyl;
$R_8$ is hydrogen, $C_{1-6}$ alkyl, $C_{3-6}$ cycloalkyl or 4-8 membered heterocyclyl, wherein the $C_{1-6}$ alkyl, $C_{3-6}$ cycloalkyl or 4-8 membered heterocyclyl is optionally substituted with one or more groups chosen from: deuterium, halogen, $C_{1-6}$ alkyl, trifluoromethyl, —OH or —NH$_2$;
$R_9$ is hydrogen or deuterium;
$R_{10}$ is hydrogen or deuterium;
n is 0, 1 or 2; provided that when n is 1, $R_3$ is not hydrogen.

Embodiment 5. The compound or the pharmaceutically acceptable salt thereof, or the solvate, the racemic mixture, the enantiomer, the diastereomer or the tautomer thereof according to any one of embodiments 1-4, wherein $X_1$ is CH or N, $X_2$ is CH, and $X_3$ is N.

Embodiment 6. The compound or the pharmaceutically acceptable salt thereof, or the solvate, the racemic mixture, the enantiomer, the diastereomer or the tautomer thereof according to any one of embodiments 1-5, wherein $X_3$ is N.

Embodiment 7. The compound or the pharmaceutically acceptable salt thereof, or the solvate, the racemic mixture, the enantiomer, the diastereomer or the tautomer thereof according to any one of embodiments 1-6, wherein both $X_1$ and $X_2$ are CH.

Embodiment 8. The compound or the pharmaceutically acceptable salt thereof, or the solvate, the racemic mixture, the enantiomer, the diastereomer or the tautomer thereof according to any one of embodiments 1-7, wherein both $Y_1$ and $Y_2$ are $CR_{10}$.

Embodiment 9. The compound or the pharmaceutically acceptable salt thereof, or the solvate, the racemic mixture, the enantiomer, the diastereomer or the tautomer thereof according to embodiment 8, wherein $R_{10}$ is hydrogen.

Embodiment 10. The compound or the pharmaceutically acceptable salt thereof, or the solvate, the racemic mixture, the enantiomer, the diastereomer or the tautomer thereof according to any one of embodiments 1-9, wherein $R_1$ and $R_2$ are each independently chosen from $C_{1-6}$ alkyl;
  preferably, $R_1$ and $R_2$ are each independently chosen from $C_{1-3}$ alkyl;
  and more preferably, both $R_1$ and $R_2$ are methyl.

Embodiment 11. The compound or the pharmaceutically acceptable salt thereof, or the solvate, the racemic mixture, the enantiomer, the diastereomer or the tautomer thereof according to any one of embodiments 1-10, wherein $R_3$ is hydrogen or halogen;
  and preferably, $R_3$ is hydrogen.

Embodiment 12. The compound or the pharmaceutically acceptable salt thereof, or the solvate, the racemic mixture, the enantiomer, the diastereomer or the tautomer thereof according to any one of embodiments 1-11, wherein preferably $R_4$ is —($C_{1-3}$ alkyl)-OH or —($C_{1-3}$ deuteroalkyl)-OH;
  preferably, $R_4$ is hydroxymethyl or hydroxy deuteromethyl;
  and more preferably, $R_4$ is hydroxymethyl.

Embodiment 13. The compound or the pharmaceutically acceptable salt thereof, or the solvate, the racemic mixture, the enantiomer, the diastereomer or the tautomer thereof according to any one of embodiments 1-12, wherein $R_3$ is hydrogen, and $R_4$ is —($C_{1-3}$ alkyl)-OH.

Embodiment 14. The compound or the pharmaceutically acceptable salt thereof, or the solvate, the racemic mixture, the enantiomer, the diastereomer or the tautomer thereof according to any one of embodiments 1-13, wherein both U and V are CH.

Embodiment 15. The compound or the pharmaceutically acceptable salt thereof, or the solvate, the racemic mixture, the enantiomer, the diastereomer or the tautomer thereof according to any one of embodiments 1-14, wherein $R_5$ is $C_{1-6}$ alkyl;
  preferably, $R_5$ is $C_{1-3}$ alkyl;
  and more preferably, $R_5$ is methyl.

Embodiment 16. The compound or the pharmaceutically acceptable salt thereof, or the solvate, the racemic mixture, the enantiomer, the diastereomer or the tautomer thereof according to any one of embodiments 1-15, wherein $Z_1$ is N, and $Z_2$, $Z_3$ and $Z_4$ are all CH.

Embodiment 17. The compound or the pharmaceutically acceptable salt thereof, or the solvate, the racemic mixture, the enantiomer, the diastereomer or the tautomer thereof according to any one of embodiments 1-16, wherein both $R_6$ and $R_7$ are methyl.

Embodiment 18. The compound or the pharmaceutically acceptable salt thereof, or the solvate, the racemic mixture, the enantiomer, the diastereomer or the tautomer thereof according to any one of embodiments 1-17, wherein $R_8$ is hydrogen, $C_{1-6}$ alkyl, $C_{3-6}$ cycloalkyl or 4-8 membered heterocyclyl, wherein the $C_{1-6}$ alkyl, $C_{3-6}$ cycloalkyl or 4-5 membered heterocyclyl is optionally substituted with one or more groups chosen from: deuterium, halogen, $C_{1-6}$ alkyl, trifluoromethyl, —OH or —$NH_2$;
  preferably, $R_8$ is hydrogen, $C_{1-6}$ alkyl or 4-5 membered heterocyclyl, wherein the $C_{1-6}$ alkyl or 4-5 membered heterocyclyl is optionally substituted with one or more groups chosen from: deuterium, halogen, $C_{1-6}$ alkyl, trifluoromethyl, —OH or —$NH_2$;
  preferably, $R_8$ is 4-5 membered heterocyclyl optionally substituted with 1 or 2 groups chosen from: deuterium, halogen, $C_{1-3}$ alkyl, trifluoromethyl, —OH or —$NH_2$;
  preferably, $R_8$ is 4-5 membered heterocyclyl;
  and more preferably, $R_8$ is 4 membered heterocyclyl.

Embodiment 19. The compound or the pharmaceutically acceptable salt thereof, or the solvate, the racemic mixture, the enantiomer, the diastereomer or the tautomer thereof according to any one of embodiments 1-18, wherein $R_8$ is oxetanyl or tetrahydrofuranyl.

Embodiment 20. The compound or the pharmaceutically acceptable salt thereof, or the solvate, the racemic mixture, the enantiomer, the diastereomer or the tautomer thereof according to embodiment 19, wherein $R_8$ is

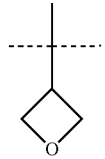

Embodiment 21. The compound of embodiment 1, or a pharmaceutically acceptable salt thereof, or a solvate, a racemic mixture, an enantiomer, a diastereomer or a tautomer thereof, which is chosen from:

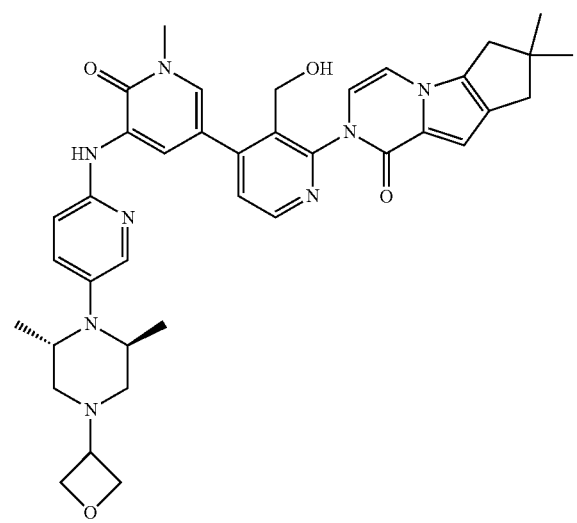

15
-continued

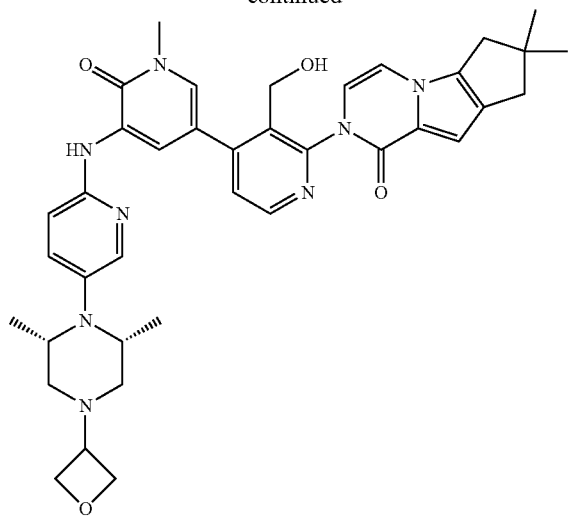

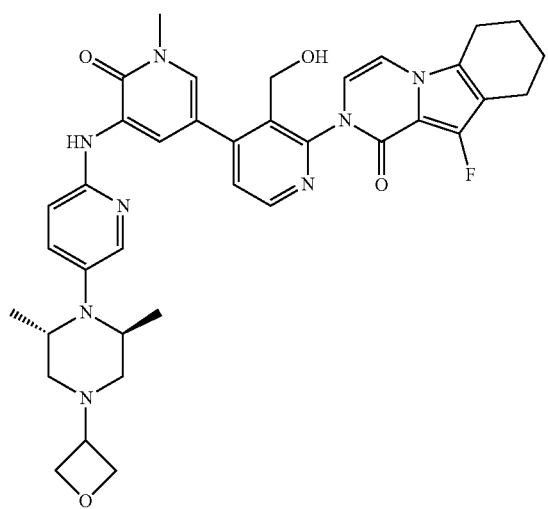 [SMILES: C[C@H]1CN(C2COC2)C[C@H](C)N1c1ccc(Nc2cc(-c3ccnc(-n4ccn5c6c(c(F)c5c4=O)CCCC6)c3CO)cn(C)c2=O)nc1]

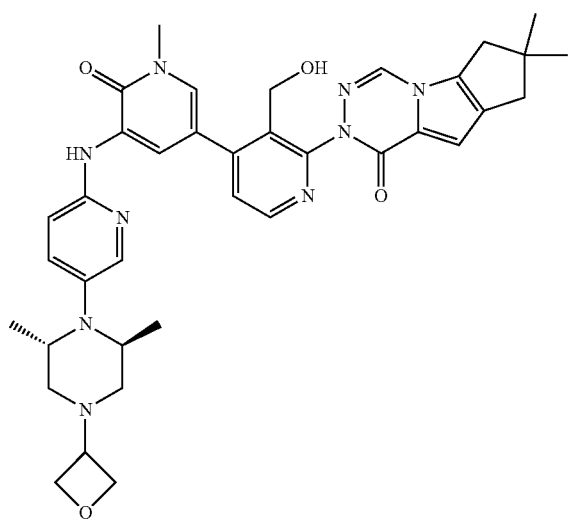

16
-continued

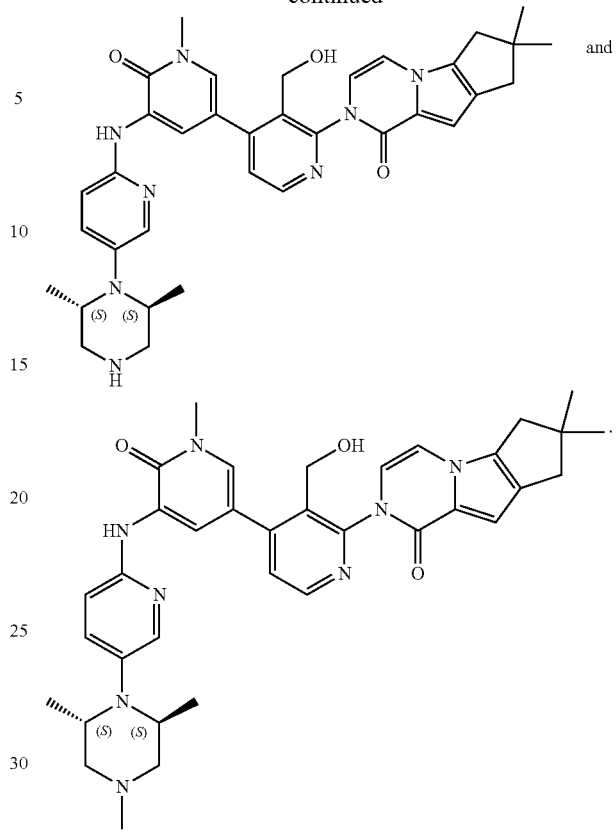

Embodiment 22. A pharmaceutical composition, comprising the compound and/or the pharmaceutically acceptable salt thereof according to any one of embodiments 1-21, and optionally comprising a pharmaceutically acceptable excipient.

Embodiment 23. A method of in vivo or in vitro inhibiting the activity of BTK, comprising contacting BTK with an effective amount of the compound and/or the pharmaceutically acceptable salt thereof according to any one of embodiments 1-21.

Embodiment 24. Use of the compound and/or the pharmaceutically acceptable salt thereof according to any one of embodiments 1-21 in the manufacture of a medicament for treating or preventing a disease mediated by BTK or at least in part by BTK, preferably for treating or preventing an autoimmune disease, an inflammatory disease or cancer, wherein the inflammatory disease or autoimmune disease is preferably chosen from: systemic inflammation and local inflammation, arthritis, rheumatoid arthritis, inflammation associated with immunosuppression, organ-graft rejection, allergic disease, ulcerative colitis, Crohn's disease, dermatitis, asthma, lupus erythematosus, Sjogren syndrome, multiple sclerosis, scleroderma, multiple sclerosis osteoporosis, idiopathic thrombocytopenic purpura, autoimmune hemolytic anemia, antineutrophil cytoplasmic antibody vasculitis, chronic obstructive pulmonary disease, psoriasis, sicca syndrome, pemphigus valgaris, diseases associated with kidney transplantation, autoimmune thyroid disease, chronic lymphocytic thyroiditis, hyperthyroidism, pernicious anemia with chronic atrophic gastritis, goodpasture syndrome, pemphigoid, primary biliary cirrhosis, acute idiopathic polyneuritis, systemic lupus erythematosus, and mixed connective tissue disease; the cancer is preferably solid tumor or hematologic malignancy, including lymphoma, leukemia and myeloma; and the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenstrom's macroglobulinaemia, marginal zone lymphoma, Burkitt's lymphoma, highly aggressive B cell non-Burkitt's lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease.

Embodiment 25. A method of treating or preventing a disease in a subject, comprising administering to the subject in need thereof an effective amount of the compound and/or the pharmaceutically acceptable salt thereof according to any one of embodiments 1-21, wherein the disease is a disease mediated by BTK or at least in part by BTK; the disease is preferably an autoimmune disease, an inflammatory disease or cancer; the inflammatory disease or autoimmune disease is preferably chosen from: systemic inflammation and local inflammation, arthritis, rheumatoid arthritis, inflammation associated with immunosuppression, organ-graft rejection, allergic disease, ulcerative colitis, Crohn's disease, dermatitis, asthma, lupus erythematosus, Sjogren syndrome, multiple sclerosis, scleroderma, multiple sclerosis osteoporosis, idiopathic thrombocytopenic purpura, autoimmune hemolytic anemia, antineutrophil cytoplasmic antibody vasculitis, chronic obstructive pulmonary disease, psoriasis, sicca syndrome, pemphigus valgaris, diseases associated with kidney transplantation, autoimmune thyroid disease, chronic lymphocytic thyroiditis, hyperthyroidism, pernicious anemia with chronic atrophic gastritis, goodpasture syndrome, pemphigoid, primary biliary cirrhosis, acute idiopathic polyneuritis, systemic lupus erythematosus, and mixed connective tissue disease; the cancer is preferably solid tumor or hematologic malignancy, including lymphoma, leukemia and myeloma; and the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenström's macroglobulinaemia, marginal zone lymphoma, Burkitt's lymphoma, highly aggressive B cell non-Burkitt's lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease.

Embodiment 26. The compound and/or the pharmaceutically acceptable salt thereof according to any one of embodiments 1-21, for use as a medicament.

Embodiment 27. The compound and/or the pharmaceutically acceptable salt thereof according to any one of embodiments 1-21, for use in treating or preventing a disease mediated by BTK or at least in part by BTK, and preferably for use in treating or preventing an autoimmune disease, an inflammatory disease or cancer, wherein the inflammatory disease or autoimmune disease is preferably chosen from: systemic inflammation and local inflammation, arthritis, rheumatoid arthritis, inflammation associated with immunosuppression, organ-graft rejection, allergic disease, ulcerative colitis, Crohn's disease, dermatitis, asthma, lupus erythematosus, Sjogren syndrome, multiple sclerosis, scleroderma, multiple sclerosis osteoporosis, idiopathic thrombocytopenic purpura, autoimmune hemolytic anemia, antineutrophil cytoplasmic antibody vasculitis, chronic obstructive pulmonary disease, psoriasis, sicca syndrome, pemphigus valgaris, diseases associated with kidney transplantation, autoimmune thyroid disease, chronic lymphocytic thyroiditis, hyperthyroidism, pernicious anemia with chronic atrophic gastritis, goodpasture syndrome, pemphigoid, primary biliary cirrhosis, acute idiopathic polyneuritis, systemic lupus erythematosus, and mixed connective tissue disease; the cancer is preferably solid tumor or hematologic malignancy, including lymphoma, leukemia and myeloma; and the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenstrom's macroglobulinaemia, marginal zone lymphoma, Burkitt's lymphoma, highly aggressive B cell non-Burkitt's lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease.

Embodiment 28. A pharmaceutical combination, comprising the compound and/or the pharmaceutically acceptable salt thereof according to any one of embodiments 1-21, and at least one additional therapeutic agent, wherein the therapeutic agent is preferably chosen from: an anti-inflammatory agent, an immunomodulator or an anti-tumor active agent, wherein the anti-tumor active agent includes a chemotherapeutic agent, an immune checkpoint inhibitor or agonist, and a targeted therapeutic agent.

The various embodiments of the present invention (including the following examples) and the features of the various embodiments should be interpreted as being arbitrarily combined with each other, and the various solutions obtained by these mutual combinations are all included in the scope of the present invention, just like the solutions obtained by listing these mutual combinations specifically and individually herein, unless clearly stated otherwise in the context.

General Synthetic Methods

The compound of formula (I) and/or a pharmaceutically acceptable salt thereof described herein can be synthesized using commercially available starting materials, by methods known in the art, or methods disclosed in the patent application. The synthetic routes shown in Scheme 1 to Scheme 2 illustrate the general synthetic methods for preparing the compounds of the present invention, and the synthetic routes shown in Scheme 3 to Scheme 6 illustrate the general synthetic methods for preparing starting material 1-1 used in Scheme 1 to Scheme 2.

Scheme 1

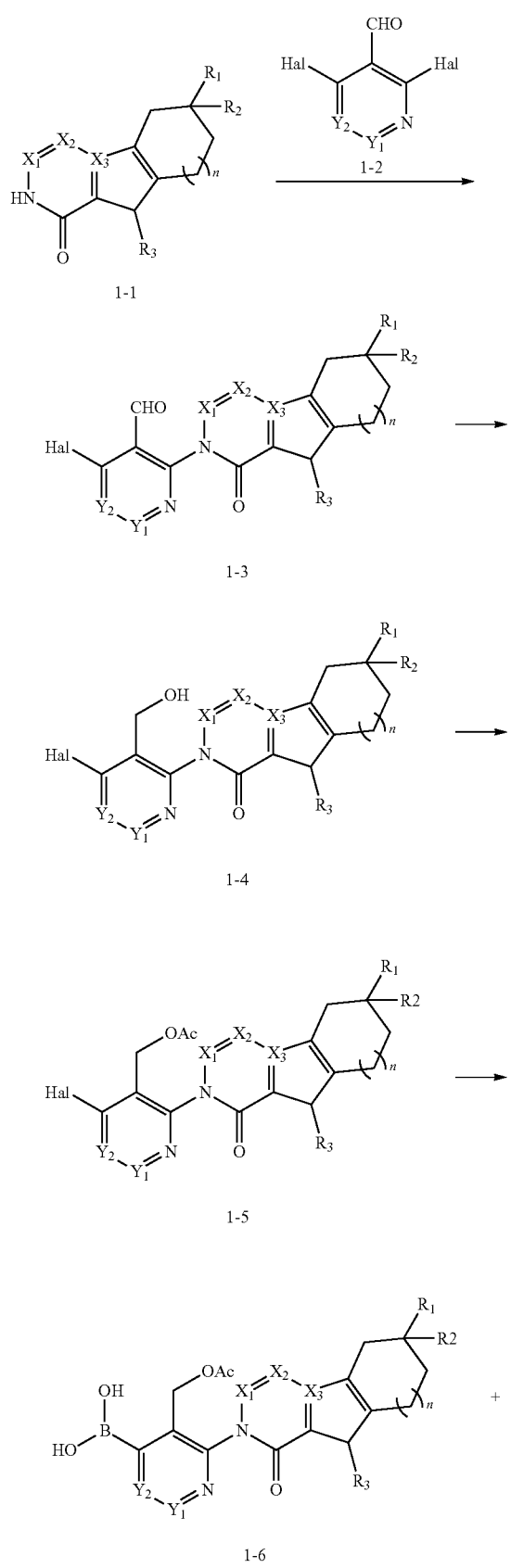

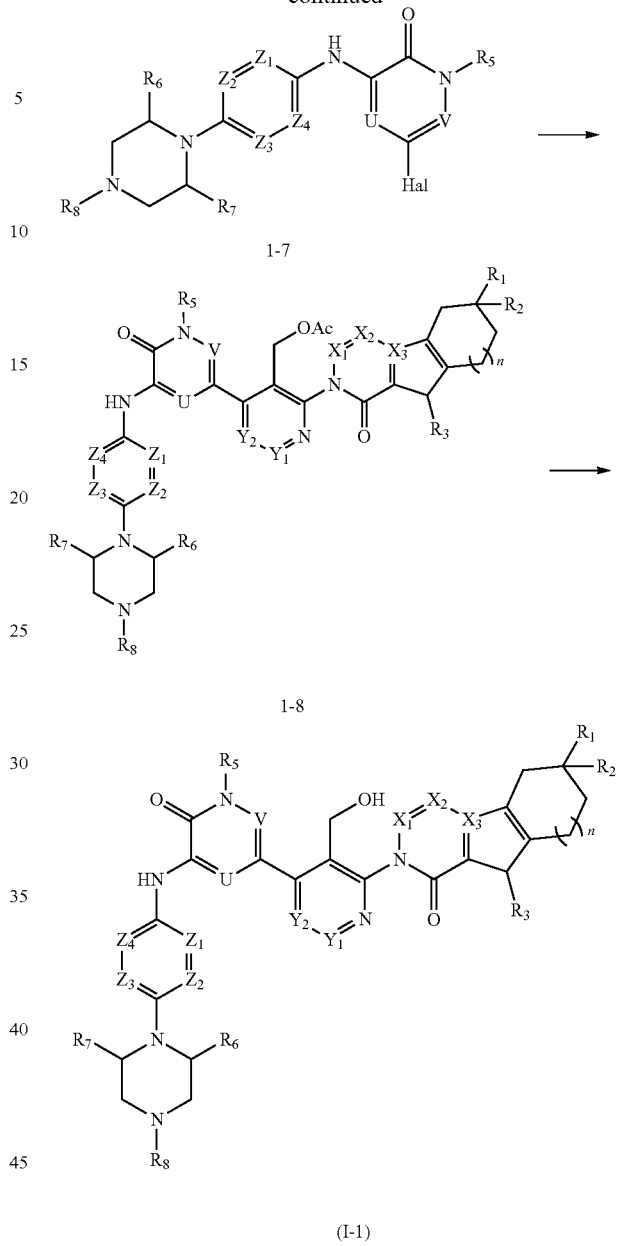

(I-1)

wherein Hal represents halogen, and $R_1$, $R_2$, $R_3$, $R_4$, $R_5$, $R_6$, $R_7$, $R_8$, $X_1$, $X_2$, $X_3$, $Z_1$, $Z_2$, $Z_3$, $Z_4$, U, V, $Y_1$, $Y_2$ and n are as defined herein.

As shown in Scheme 1, a compound of formula 1-1 is reacted with a dihaloarylaldehyde compound of formula 1-2 under the catalysis of cuprous iodide to obtain a compound of formula 1-3. The carbon-nitrogen coupling reaction catalyzed by cuprous iodide is carried out under suitable conditions. The solvent used can be chosen from a polar solvent such as 1,4-dioxane and DMF, and the base used can be chosen from $Cs_2CO_3$, $Na_2CO_3$, $K_3PO_4$, etc. Under suitable conditions, a compound of formula 1-4 of the present invention is obtained by reducing the compound of formula 1-3. The reducing agent used can be chosen from sodium borohydride, potassium borohydride, lithium borohydride, etc., and the solvent used can be chosen from a polar solvent, such as methanol, ethanol or a mixed solvent of methanol and dichloromethane. A compound of formula 1-5 is obtained by acetylating the compound of formula 1-4. The compound of formula 1-5 is reacted with bis(pinacolato)diboron under suitable conditions to obtain a boracic acid or boronic acid ester compound of formula 1-6. The compound of formula 1-6 is reacted with a halide of formula 1-7 by Suzuki coupling reaction under the catalysis of appropriate palladium reagent to obtain a compound of formula 1-8. Palladium catalyzed carbon-carbon coupling reaction is carried out under suitable conditions. The solvent used can be chosen from a polar solvent such as 1,4-dioxane, DMF, THF or a mixed solvent of 1,4-dioxane and water; the base used can be chosen from $Cs_2CO_3$, $Na_2CO_3$, $K_3PO_4$, etc.; and the catalyst used can be chosen from $Pd(dppf)Cl_2 \cdot CH_2Cl_2$, $Pd(PPh_3)_4$, $Pd(OAc)_2$, etc. A compound of formula (I-1) of the present invention is obtained by deacetylating the compound of formula 1-8 under appropriate alkaline conditions. The base used can be chosen from potassium carbonate, sodium carbonate, lithium hydroxide, etc., and the solvent used can be chosen from a polar solvent, such as methanol, ethanol or a mixed solvent of methanol and water.

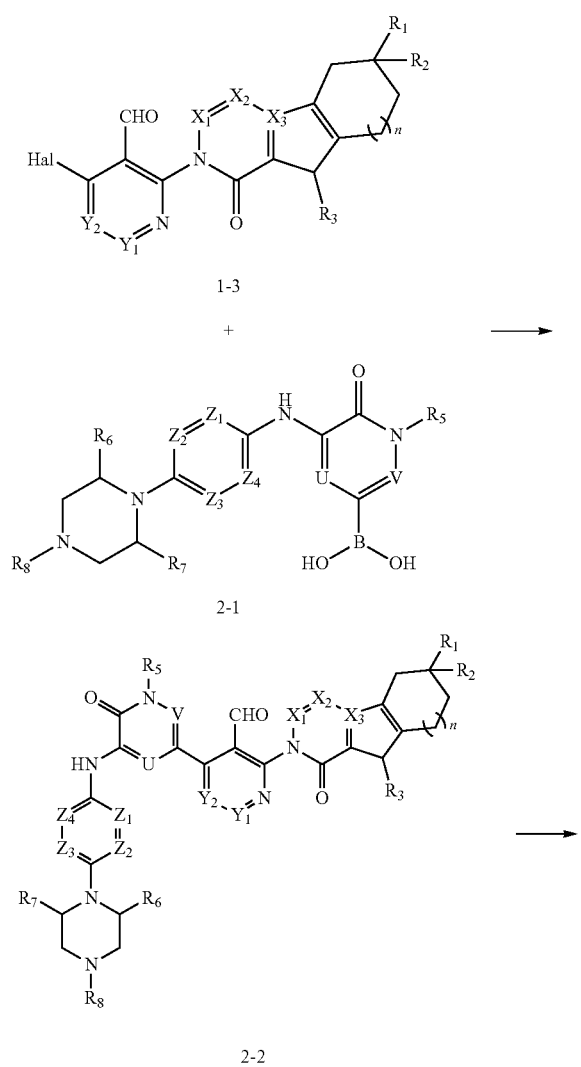

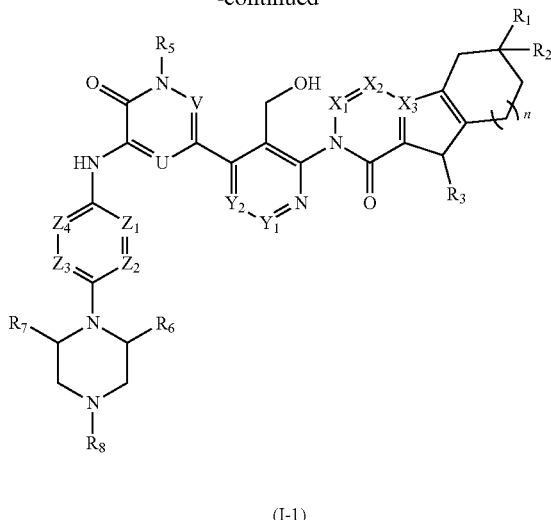

As shown in Scheme 2, the compound of formula 1-3 is reacted with a boracic acid or boric acid ester of formula 2-1 by Suzuki coupling reaction under the catalysis of appropriate palladium reagent to obtain a compound of formula 2-2. Palladium catalyzed carbon-carbon coupling reaction is carried out under suitable conditions. The solvent used can be chosen from a polar solvent such as 1,4-dioxane, DMF, THF or a mixed solvent of 1,4-dioxane and water; the base used can be chosen from $Cs_2CO_3$, $Na_2CO_3$, $K_3PO_4$, etc.; and the catalyst used can be chosen from $Pd(dppf)Cl_2\text{-}CH_2Cl_2$, $Pd(PPh_3)_4$, $Pd(OAc)_2$, etc. Under suitable conditions, the compound of formula (I-1) of the present invention is obtained by reducing the compound of formula 2-2. The reducing agent used can be chosen from sodium borohydride, potassium borohydride, lithium borohydride, etc., and the solvent used can be chosen from a polar solvent, such as methanol, ethanol or a mixed solvent of methanol and dichloromethane.

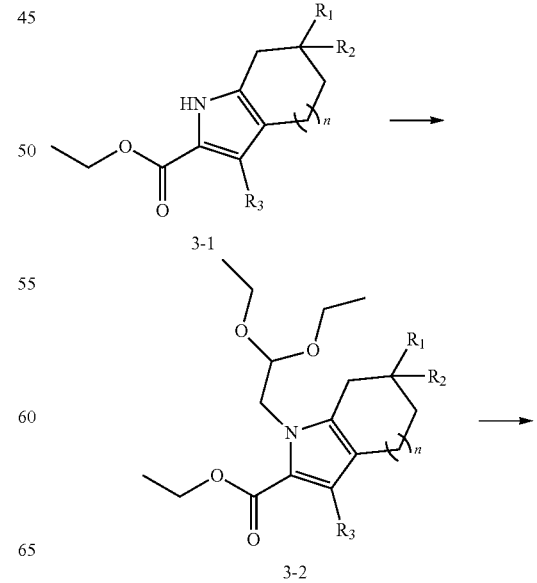

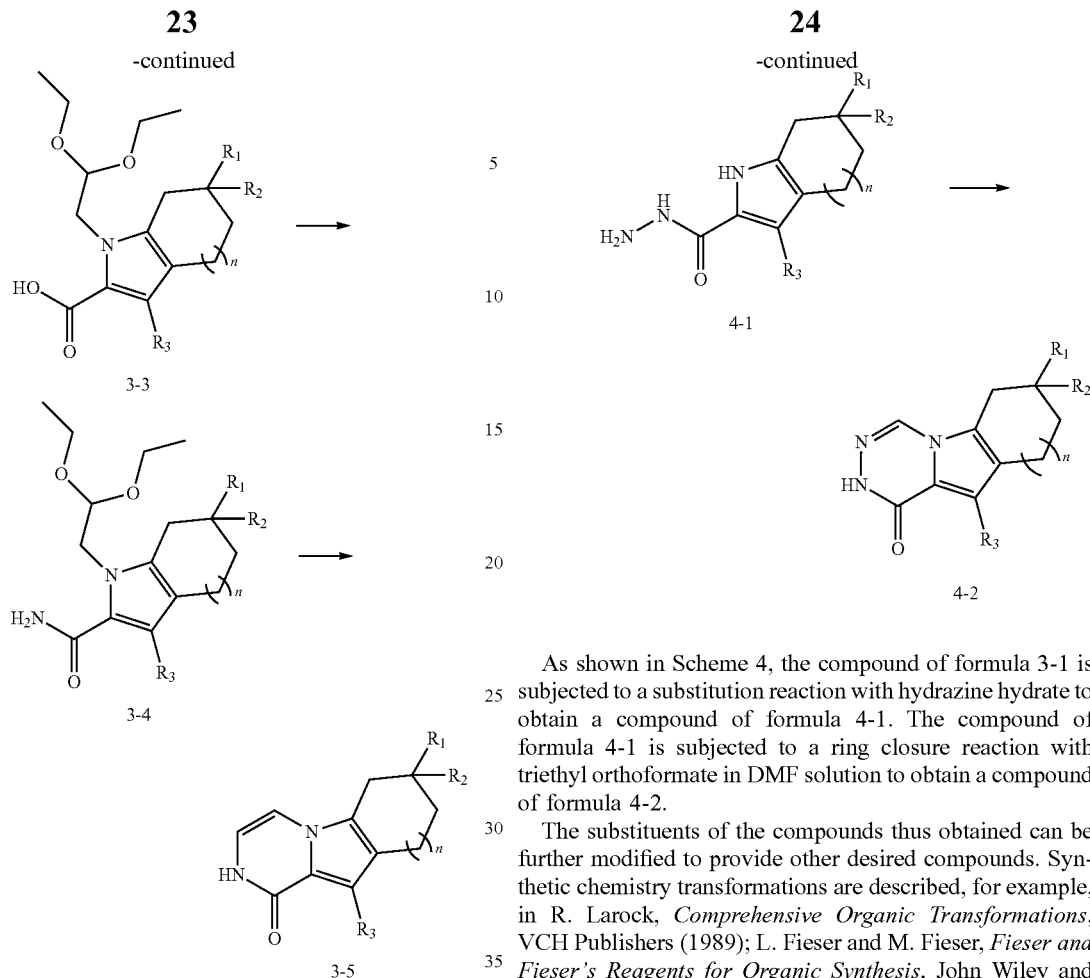

3-3

3-4

3-5

As shown in Scheme 3, the compound of formula 3-1 is subjected to a substitution reaction with bromoacetaldehyde diethyl acetal under suitable conditions to obtain a compound of formula 3-2. The base used can be chosen from cesium carbonate, etc., and the solvent used can be chosen from a polar solvent such as DMF and 1,4-dioxane. The compound of formula 3-2 is hydrolyzed in an alkaline solution to obtain a compound of formula 3-3. The base used can be chosen from lithium hydroxide, potassium carbonate, sodium carbonate, etc.; and the solvent used can be chosen from a polar solvent, such as methanol, ethanol or a mixed solvent of methanol and water. The compound of formula 3-3 is subjected to a condensation reaction with HATU and aqueous ammonia to obtain a compound of formula 3-4. The compound of formula 3-4 is subjected to ring closure in acetic acid to obtain a compound of formula 3-5.

Scheme 4

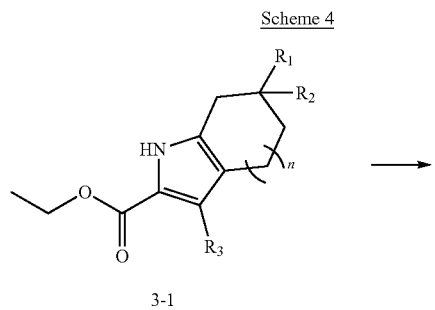

3-1

4-1

4-2

As shown in Scheme 4, the compound of formula 3-1 is subjected to a substitution reaction with hydrazine hydrate to obtain a compound of formula 4-1. The compound of formula 4-1 is subjected to a ring closure reaction with triethyl orthoformate in DMF solution to obtain a compound of formula 4-2.

The substituents of the compounds thus obtained can be further modified to provide other desired compounds. Synthetic chemistry transformations are described, for example, in R. Larock, *Comprehensive Organic Transformations*, VCH Publishers (1989); L. Fieser and M. Fieser, *Fieser and Fieser's Reagents for Organic Synthesis*, John Wiley and Sons (1994); L. Paquette, ed., *Encyclopedia of Reagents for Organic Synthesis*, John Wiley and Sons (1995) and subsequent editions thereof.

Before use, the compound(s) of the present invention can be purified by column chromatography, high performance liquid chromatography, crystallization or other suitable methods.

Pharmaceutical Compositions and Utility

The compound of the present invention herein (e.g., a compound of any of the embodiments as described herein) is used, alone or in combination with one or more additional therapeutic agents, to formulate pharmaceutical compositions. A pharmaceutical composition comprises: (a) an effective amount of the compounds of the present invention; (b) a pharmaceutically acceptable excipient (e.g., one or more pharmaceutically acceptable carriers); and optionally (c) at least one additional therapeutic agent.

A pharmaceutically acceptable excipient refers to an excipient that is compatible with active ingredients of the composition (and in some embodiments, capable of stabilizing the active ingredients) and not deleterious to the subject to be treated. For example, solubilizing agents, such as cyclodextrins (which form specific, more soluble complexes with the compounds of the present invention), can be utilized as pharmaceutical excipients for delivery of the active ingredients. Examples of other excipients or carries include colloidal silicon dioxide, magnesium stearate, cellulose, sodium lauryl sulfate, and pigments such as D & C Yellow #10. Suitable pharmaceutically acceptable excipients are disclosed in Remington's Pharmaceutical Sciences, A. Osol, a standard reference text in the art.

A pharmaceutical composition comprising a compound of the present invention herein can be administered in various known manners, such as orally, topically, rectally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A pharmaceutical composition described herein can be prepared in the form of tablet, capsule, sachet, dragee, powder, granule, lozenge, powder for reconstitution, liquid preparation, or suppository. In some embodiments, a pharmaceutical composition comprising a compound of the present invention herein is formulated for intravenous infusion, topical administration, or oral administration.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In some embodiments, the compound of the present invention can be present in an amount of 1, 5, 10, 15, 20, 25, 50, 75, 80, 85, 90, 95, 100, 125, 150, 200, 250, 300, 400 and 500 mg in a tablet. In some embodiments, the compound of the present invention can be present in an amount of 1, 5, 10, 15, 20, 25, 50, 75, 80, 85, 90, 95, 100, 125, 150, 200, 250, 300, 400 and 500 mg in a capsule.

A sterile injectable composition (e.g., aqueous or oleaginous suspension) can be formulated according to techniques known in the art using suitable dispersing or wetting agents (for example, Tween 80) and suspending agents. The sterile injectable composition can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives, and natural pharmaceutically acceptable oils, such as olive oil or castor oil, especially in their polyoxyethylated versions, can be used as sterile injectable medium. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes, by weight, about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

Suitable in vitro assays can be used to evaluate the effect of the compounds of the present invention in inhibiting the activity of BTK. The compounds of the present invention can further be examined for additional effects in preventing or treating cancer by in vivo assays. For example, the compound of the present invention can be administered to an animal (e.g., a mouse model) having cancer and its therapeutic effects can be accessed. If the pre-clinical results are successful, the dosage range and administration route for animals, such as humans, can be projected.

The compound of the present invention can be shown to have sufficient pre-clinical practical utility to merit clinical trials hoped to demonstrate a beneficial therapeutic or prophylactic effect, for example, in subjects with cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and hematologic malignancies, such as leukemia, lymphoma or myeloma. The term "cancer" encompasses diseases of skin, tissues, organs, bone, cartilage, blood, and vessels. The term "cancer" further encompasses primary cancer, and metastatic cancer, recurrent cancer and refractory cancer.

Non-limiting examples of solid tumors include pancreatic cancer; bladder cancer; colorectal cancer; breast cancer, including metastatic breast cancer; prostate cancer, including androgen-dependent and androgen-independent prostate cancer; testicular cancer; renal cancer, including, e.g., metastatic renal cell carcinoma; urothelial carcinoma; liver cancer; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; endometrial cancer; gastric cancer; esophageal cancer; head and neck cancer, including, e.g., squamous cell carcinoma of the head and neck; skin cancer, including, e.g., melanoma and basal carcinoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; sarcoma, including, e.g., Kaposi's sarcoma; adrenal carcinoma; mesothelial carcinoma; choriocarcinoma; muscle carcinoma; connective tissue carcinoma; and thyroid carcinoma.

Non-limiting examples of hematologic malignancies include acute myelogenous leukemia (AML); chronic myelogenous leukemia (CML), including accelerated phase CML and CML blastic phase (CML-BP); acute lymphocytic leukemia (ALL); chronic lymphocytic leukemia (CLL), including high risk CLL; human acute monocytic leukemia (M(5)); hairy cell leukemia; lymphocytic leukemia; chronic lymphoid leukemia; myelogenous leukemia; myelodysplastic syndrome or acute lymphoblastic leukemia; small lymphotic lymphoma (SLL), lymphoblastic lymphoma, and Hodgkin's lymphoma; non-Hodgkin's lymphoma (NHL); follicular lymphoma; mantle cell lymphoma (MCL); B-cell lymphoma; T cell lymphoma; diffuse large B-cell lymphoma (DLBCL); large B-cell lymphoma (LBCL); follicular lymphoma, marginal zone lymphoma, Burkitt's lymphoma, non-Burkitt's highly degree B cell malignant lymphoma, extranodal marginal-zone B-cell lymphoma; multiple myeloma (MM); Waldenstrom's macroglobulinaemia; myelodysplastic syndrome (MDS), including refractory anemia (RA), refractory anemia with ring sideroblasts (RARS), refractory anemia with excess of blast (RAEB) and refractory anemia with excess blasts in transformation (RAEB-T); and myeloproliferative syndrome.

In some embodiments, hematologic malignancy is recurrent or refractory diffuse large B-cell lymphoma (DLBCL), recurrent or refractory mantle cell lymphoma, recurrent or refractory follicular lymphoma, recurrent or refractory CLL, recurrent or refractory SLL, and recurrent or refractory multiple myeloma.

The compound of the present invention can be used to achieve a beneficial therapeutic or prophylactic effect, for example, in subjects with cancer.

The compound of the present invention can be used to achieve a beneficial therapeutic or prophylactic effect, for example, in subjects with an autoimmune disease, or in subjects with inflammatory diseases.

The term "autoimmune disease" refers to a disease or disorder arising from and/or directed against an individual's own tissues or organs, or a co-segregate or manifestation thereof, or resulting condition therefrom. Examples of autoimmune diseases include, but are not limited to: chronic obstructive pulmonary disease (COPD), allergic rhinitis, lupus erythematosus, myasthenia gravis, Sjogren syndrome, multiple sclerosis (MS), scleroderma (also referred to as systemic sclerosis), multiple sclerosis osteoporosis, arthritis (such as rheumatoid arthritis (RA), and collagen-induced arthritis), psoriasis, inflammatory bowel disease (such as ulcerative colitis and Crohn's disease), asthma, idiopathic thrombocytopenic purpura, autoimmune hemolytic anemia, antineutrophil cytoplasmic antibody vasculitis, sicca syndrome, pemphigus valgaris, diseases associated with kidney transplantation and myeloproliferative disease, such as myelofibrosis, and post-polycythemia vera/essential thrombocytosis myelofibrosis (post-PV/ET myelofibrosis), autoimmune thyroid disease, chronic lymphocytic thyroiditis, hyperthyroidism, pernicious anemia with chronic atrophic gastritis, goodpasture syndrome, pemphigoid, primary biliary cirrhosis, acute idiopathic polyneuritis, systemic lupus erythematosus, mixed connective tissue disease, etc. In some embodiment, autoimmune disease is chosen from arthritis, such as, rheumatoid arthritis (RA), collagen induced arthritis, and the like.

The term "inflammatory disease" or "inflammatory condition" refers to a pathological state that leads to inflammation, especially due to neutrophil chemotaxis. Non-limiting examples of inflammatory diseases include systemic inflammation and local inflammation, inflammation associated with immunosuppression, organ-graft refection, allergic disease, inflammatory skin disease (including psoriasis and atopic dermatitis); systemic scleroderma and sclerosis; reactions associated with inflammatory bowel diseases (IBD, such as Crohn's disease and ulcerative colitis); ischemia reperfusion injury, including reperfusion injury of tissue caused by surgery, myocardial ischemia, such as myocardial infarction, cardiac arrest, reperfusion after heart operation and abnormal contractile response of coronary vessel after percutaneous transluminal coronary angioplasty, surgical tissue reperfusion injury of stroke and abdominal aortic aneurysm; cerebral edema secondary to stroke; cranial injury, and hemorrhagic shock; suffocation; adult respiratory distress syndrome; acute lung injury; Behcet's disease; dermatomyositis; polymyositis; multiple sclerosis (MS); dermatitis; meningitis; encephalitis; uveitis; osteoarthritis; lupus nephritis; autoimmune disease such as rheumatoid arthritis (RA), Sjorgen's syndrome, and vasculitis; diseases involving leukopedesis; septicemia or central nervous system (CNS) inflammatory disease secondary to trauma, and multiple organ injury syndrome; alcoholic hepatitis; bacterial pneumonia; antigen-antibody complex mediated disease, including glomerulonephritis; pyaemia; sarcoidosis; immunopathologic responses to tissue/organ transplantation; lung inflammation, including pleurisy, alveolitis, vasculitis, pneumonia, chronic bronchitis, bronchiectasia, diffuse panbronchiolitis, hypersensitivity pneumonitis, idiopathic pulmonary fibrosis (IPF), cystic fibrosis, etc. Preferably indications include, but are not limited to, chronic inflammation, autoimmune diabetes, rheumatoid arthritis (RA), rheumatoid spondylitis, gouty arthritis and other arthrosis conditions, multiple sclerosis (MS), asthma, systemic lupus erythematosus, adult respiratory distress syndrome, Behcet's disease, psoriasis, chronic pulmonary inflammatory disease, graft versus host reaction, Crohn's disease, ulcerative colitis, inflammatory bowel disease (IBD), Alzheimer's disease and pyresis, and any diseases associated with inflammation and related conditions.

In addition, the compounds of the present invention (e.g., a compound of any of the examples as described herein) can be administered in combination with additional therapeutic agents for the treatment of diseases or disorders described herein, such as an autoimmune disease, an inflammatory disease or cancer. The additional active ingredients may be administered separately with the compound of the present invention or included with such an ingredient in a pharmaceutical composition according to the disclosure, such as a fixed-dose combination drug product. In some embodiments, additional active ingredients are those that are known or discovered to be effective in the treatment of diseases mediated by BTK or at least in part by BTK, such as another BTK inhibitor or a compound active against another target associated with the particular disease. The combination may serve to increase efficacy (e. g., by including in the combination a compound potentiating the potency or effectiveness of the compound of the present invention), decrease one or more side effects, or decrease the required dose of the compound of the present invention.

In some embodiments, the compounds of the present invention (such as any compound herein) can be administered in combination with additional therapeutic agents, such as anti-inflammatory agents, immunomodulators or anti-tumor active agents, wherein the anti-tumor active agents include chemotherapeutic agents, immune checkpoint inhibitors or agonists, and targeted therapeutic agents. The term "anti-tumor active agent" as used herein refers to any agent that is administered to a subject suffering from cancer for the purposes of treating the cancer, such as a chemotherapeutic agent, an immune checkpoint inhibitor or agonist, and a targeted therapeutic agent.

Non-limiting examples of anti-inflammatory agents and immunomodulators include immunosuppressants (e.g., tacrolimus, cyclosporin, rapamycin, methotrexate, cyclophosphamide, azathioprine, mercaptopurine, mycophenolate or FTY720), glucocorticoids (e.g., prednisone, cortisone acetate, prednisolone, methylprednisolone, dexamethasone, betamethasone, triamcinolone, hydroxyprednisolone, beclomethasone, fludrocortisone acetate, deoxycorticosterone acetate and aldosterone), non-steroidal anti-inflammatory drugs (e.g., salicylates, arylalkanoic acids, 2-arylpropionic acids, N-arylanthranilic acids, oxicams, coxibs or thiobenzanilide), cyclooxygenase-2-specific inhibitors (e.g., valdecoxib, celecoxib or rofecoxib), leflunomide, gold thioglucose, gold thiomalate, moclobemide, sulfasalazine, hydroxychloroquine, minocycline, TNF-α binding proteins (e.g., infliximab, etanercept or adalimumab), abatacept, anakinra, interferons, interferon-Y, interleukin-2, interleukin-6, interleukin-12/23, interleukin-17 antibody drugs, allergy vaccines, antihistamines, antileukotrienes, β-agonists, theophylline or anticholinergics; JAK3 kinase inhibitors, including all known JAK3 kinase inhibitors, but not limited to Tofactinib; IRAK4 inhibitors, RIPK1 inhibitors, etc.

Non-limiting examples of chemotherapeutic agents include topoisomerase I inhibitors (e. g., irinotecan, topotecan, camptothecin and analogs or metabolites thereof, and doxorubicin); topoisomerase II inhibitors (e. g., etoposide, teniposide, mitoxantrone, idarubicin, and daunorubicin); alkylating agents (e. g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e. g., cisplatin, oxaliplatin, and carboplatin); and free radical generators such as bleomycin; nucleoside mimetics (e.g., 5-fluorouracil, capecitabine, gemcitabine, fludarabine, cytarabine, azacitidine, mercaptopurine, thioguanine, pentostatin, and hydroxyurea); paclitaxel, docetaxel, and related analogs; vincristine, vinblastin, and related analogs; thalidomide and related analogs (e. g., CC-5013 and CC-4047).

Non-limiting examples of immune checkpoint inhibitors or agonists include PD-1 inhibitors, for example, anti-PD-1 antibodies, such as pembrolizumab and nivolumab; PD-L1 inhibitors, for example, anti-PD-L1 antibodies, such as atezolizumab, durvalumab, and avelumab; CTLA-4 inhibitors, such as ipilimumab; and BTLA inhibitors, LAG-3 inhibitors, TIM3 inhibitors, TIGIT inhibitors, VISTA inhibitors, OX-40 agonists, and the like.

Targeted therapeutic agents include various small molecule or macromolecular targeted therapeutic agents, and non-limiting examples thereof include: protein tyrosine kinase inhibitors (such as imatinib mesylate and gefitinib); proteasome inhibitors (such as bortezomib); NF-κB inhibitors, including IKB kinase inhibitors; PI3K$_6$ inhibitors; SYK inhibitors; Bcl2 inhibitors; antibodies that bind to proteins overexpressed in cancer to down-regulate cell replication, such as anti-CD20 antibody (such as rituximab, ibritumomab tiuxetan, and tositumomab), anti-Her2 monoclonal antibody (trastuzumab), anti-EGFR antibody (cetuximab) and anti-VEGFR antibody (bevacizumab); anti-angiogenic drugs, such as lenalidomide; and other protein or enzyme inhibitors, these proteins or enzymes are known to be upregulated, overexpressed or activated in cancers, and the inhibiting on them can down-regulate cell replication.

EXAMPLES

The examples below are intended to be purely exemplary and should not be considered to be limiting in any way.

Efforts have been made to ensure the accuracy with respect to numbers used (for example, amounts, temperature, etc.), but those skilled in the art should understand that some experimental errors and deviations should be accounted for. Unless indicated otherwise, parts are parts by weight, temperature is in degrees Centigrade, and pressure is at or near atmospheric. All MS data were determined by Agilent 6120 or Agilent 1100. All NMR data were generated using a Varian 400 MR machine. All reagents and starting materials, except synthesized intermediates, used in the present invention are commercially available. Positive control GDC-0853 (fenebrutinib) was purchased from Shanghai Linkchem Medical Technology Co., Ltd. All compound names except the reagents are generated by Chemdraw 16.0.

If there is any atom with empty valence(s) in any one of the structures disclosed herein, the empty balance(s) is (are) the hydrogen atom(s) which is (are) omitted for convenience purpose.

In the present application, in the case of inconsistency of the name and structure of a compound, when the two of which are both given for the compound, it is subject to the structure of the compound, unless the context shows that the structure of the compound is incorrect, and the name is correct.

In the following examples, the abbreviations are used:
CD$_3$OD Deuterated methanol
DCM Dichloromethane
DIEA N,N-diisopropylethylamine
DMF N,N-dimethylformamide
DMSO Dimethyl sulfoxide
DMSO-d$_6$ Deuterated dimethyl sulfoxide
g Gram
HATU 2-(7-azabenzotriazole)-N,N,N',N'-tetramethyluronium hexafluorophosphate
HPMC Hydroxypropyl methylcellulose
L Liter
M Mole/liter
mg Milligram
mL Milliliter
mmol Millimole
mol Mole
NBS N-bromosuccinimide
Pd$_2$(dba)$_3$ Tris(dibenzylidene acetone)dipalladium
Pd(dppf)Cl$_2$ CH$_2$Cl$_2$ [1,1'-bis(diphenylphosphino) ferrocene]palladium dichloride dichloromethane complex
Xphos 2-dicyclohexylphosphine-2',4',6'-triisopropyl biphenyl
Xant-phos 4,5-bis(diphenylphosphino)-9,9-dimethylxanthene Example 1 Synthesis of Compounds Intermediate I-1

3-((5-((2S,6S)-2,6-dimethyl-4-(oxetan-3-yl)piperazin-1-yl)pyridin-2-yl)amino)-1-methyl-5-(4,4,5,5-tetramethyl-1,3,2-dioxaborolan-2-yl)pyridin-2(1H)-one

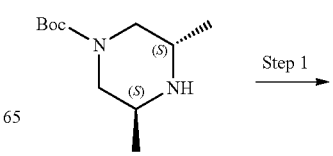

Step 1

31

-continued

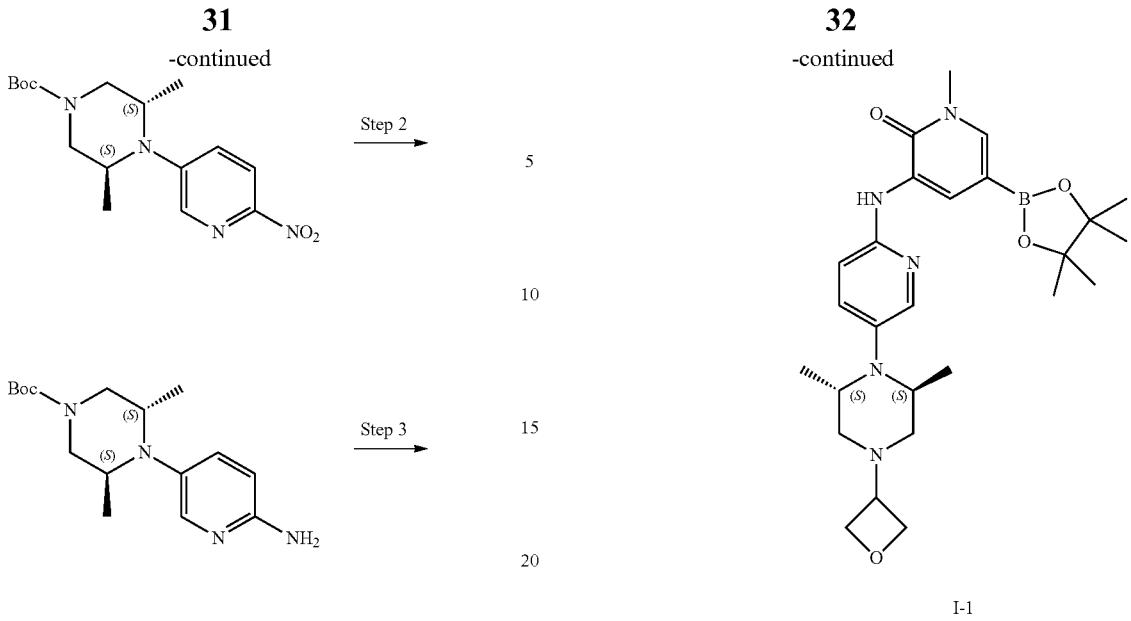

32

-continued

I-1

Step 1: tert-butyl (3S,5S)-3,5-dimethyl-4-(6-nitropyridin-3-yl)piperazine-1-carboxylate Under nitrogen, to a solution of 5-fluoro-2-nitropyridine (4.5 g, 31.7 mmol) and tert-butyl (3S,5S)-3,5-dimethylpiperazine-1-carboxylate (5.0 g, 23.3 mmol) in DMSO (40 mL) was added DIEA (40 mL). The mixture was reacted at 120° C. for 24 hours, and then cooled to room temperature, and concentrated in vacuum under reduced pressure, and the resulting residue was purified with silica gel column chromatography (dichloromethane/ethyl acetate) to give the target product (6.0 g, yield 77%). [M+H]$^+$ 337.1

Step 2: tert-butyl (3S,5S)-4-(6-aminopyridin-3-yl)-3,5-dimethylpiperazine-1-carboxylate At room temperature, a mixture of tert-butyl (3S,5S)-3,5-dimethyl-4-(6-nitropyridin-3-yl)piperazine-1-carboxylate (4.5 g, 13.4 mmol) and 10% palladium-carbon (with 50% water, 3.0 g) in methanol (100 mL) was introduced with hydrogen, and the mixture was reacted at 40° C. for 3 hours. The reaction solution was filtered, and the filtrate was collected, and concentrated in vacuum under reduced pressure to give the target product (3.9 g, yield 95%), which was directly used in the next step. [M+H]$^+$ 307.2

Step 3: tert-butyl (3S,5S)-4-(6-((5-bromo-1-methyl-2-oxo-1,2-dihydropyridin-3-yl)amino)pyridin-3-yl)-3,5-dimethylpiperazine-1-carboxylate Under nitrogen, to a solution of tert-butyl (3S,5S)-4-(6-aminopyridin-3-yl)-3,5-dimethylpiperazine-1-carboxylate (3.0 g, 9.8 mmol) and 3,5-dibromo-1-methylpyridin-2(1H)-one (2.0 g, 7.5 mmol) in 1,4-dioxane (100 mL) were added Xant-phos (433 mg, 0.75 mmol), Pd$_2$(dba)$_3$ (343 mg, 0.375 mmol) and cesium carbonate (4.9 g, 15.0 mmol). The mixture was reacted at 90° C. for 12 hours, and then cooled to room temperature, and filtered; the filtrate was collected and concentrated; and the resulting residue was purified with silica gel column chromatography (methanol/dichloromethane) to give the target product (3.0 g, yield 81%). [M+H]$^+$ 492.1, 494.1

Step 4: 5-bromo-3-((5-(((2S,6S)-2,6-dimethyl-4-(oxetan-3-yl)piperazin-1-yl)pyridin-2-yl)amino)-1-methylpyridin-2(1H)-one To a solution of tert-butyl (3S,5S)-4-(6-((5-bromo-1-methyl-2-oxo-1,2-dihydropyridin-3-yl)amino)pyridin-3-yl)-3,5-dimethylpiperazine-1-carboxylate (3.0 g, 6.1 mmol) in methanol (15 mL) was added concentrated hydrochloric acid (8 mL), and the mixture was stirred at 50° C. for 30 minutes.

The reaction solution was concentrated in vacuum under reduced pressure, and to a solution of the resulting residue in methanol (30 mL) was added a suspension of zinc chloride (2.5 g, 18.3 mmol) and sodium cyanoborohydride (2.3 g, 36.6 mmol) in methanol (50 mL). The reaction was stirred at 50° C. for 4 hours, and concentrated in vacuum under reduced pressure, and the resulting residue was purified with silica gel column chromatography (methanol/water) to give the target product (2.0 g, yield 73%). [M+H]$^+$ 448.1, 450.1

Step 5: 3-((5-(((2S,6S)-2,6-dimethyl-4-(oxetan-3-yl)piperazin-1-yl)pyridin-2-yl)amino)-1-methyl-5-(4,4,5,5-tetramethyl-1,3,2-dioxaborolan-2-yl)pyridin-2(1H)-one Under nitrogen, to a solution of 5-bromo-3-((5-((2S,6S)-2,6-dimethyl-4-(oxetan-3-yl)piperazin-1-yl)pyridin-2-yl)amino)-1-methylpyridin-2(1H)-one (1.2 g, 2.68 mmol) and bis(pinacolato)diboron (1.7 g, 6.7 mmol) in 1,4-dioxane (60 mL) were added Xphos (128 mg, 0.27 mmol), Pd$_2$(dba)$_3$ (247 mg, 0.27 mmol) and potassium acetate (784 mg, 8.0 mmol). The mixture was reacted at 65° C. for 6 hours, and then cooled to room temperature, and filtered; the filtrate was collected, and concentrated in vacuum under reduced pressure; and the resulting residue was purified with silica gel column chromatography (methanol/dichloromethane) to give the target compound (650 mg, purity 50%, yield 24%). [M+H]$^+$ 496.3

The intermediates in the table below were prepared by following the steps for preparing intermediate I-1 from corresponding starting materials and reagents:

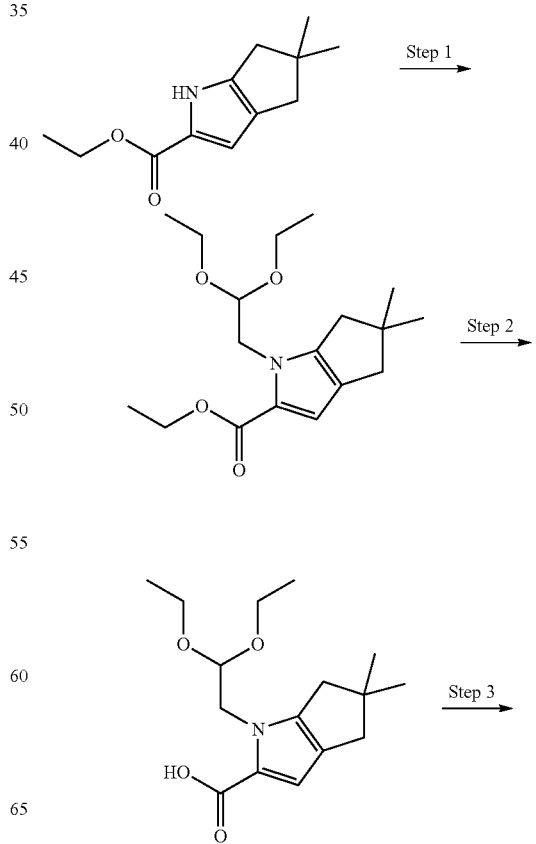

| Intermediates | Structural formula | LC-MS [M + H]$^+$ |
|---|---|---|
| I-2 | | 496.3 |
| I-6 | | 492.1, 494.1 |

Intermediate I-3

4-chloro-2-(7,7-dimethyl-1-oxo-1,6,7,8-tetrahydro-2H-cyclopenta[4,5]pyrrolo[1,2-a]pyrazin-2-yl)nicotinaldehyde

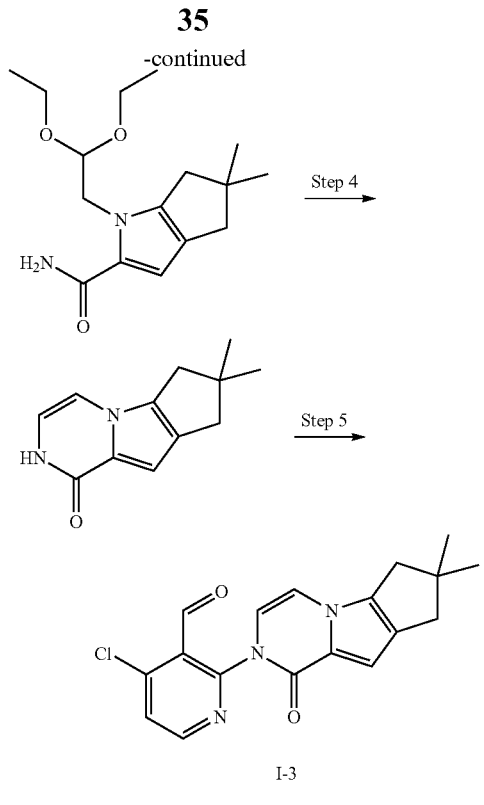

Step 1: ethyl 1-(2,2-diethoxyethyl)-5,5-dimethyl-1,4,5,6-tetrahydrocyclopenta[b]pyrrole-2-carboxylate To a solution of ethyl 5,5-dimethyl-1,4,5,6-tetrahydrocyclopenta[b]pyrrole-2-carboxylate (20.0 g, 96 mmol) in DMF (120 mL) were added cesium carbonate (80.0 g, 245 mmol) and bromoacetaldehyde diethyl acetal (40.0 g, 203 mmol), and the mixture was reacted at 100° C. for 16 hours. Water (200 mL) was added to the reaction solution, and the mixture was extracted with ethyl acetate (200 mL×2). The organic phase was collected and combined, and concentrated in vacuum under reduced pressure, and the resulting residue was purified with silica gel column chromatography (petroleum ether/ethyl acetate) to give the target product (31.0 g, yield 100%). [M+Na]+324.1

Step 2: 1-(2,2-diethoxyethyl)-5,5-dimethyl-1,4,5,6-tetrahydrocyclopenta[b]pyrrole-2-carboxylic acid To a solution of ethyl 1-(2,2-diethoxyethyl)-5,5-dimethyl-1,4,5,6-tetrahydrocyclopenta[b]pyrrole-2-carboxylate (31.0 g, 96 mmol) in ethanol (150 mL) and water (150 mL) was added lithium hydroxide monohydrate (14.2 g, 338 mmol), and the mixture was reacted at 80° C. for 12 hours. Ethanol was removed in vacuum under reduced pressure, and the pH was adjusted to 5-6 with concentrated hydrochloric acid under ice bath cooling. Water (200 mL) was added, and the mixture was extracted with ethyl acetate (200 mL×3). The organic phase was collected and combined, dried over anhydrous sodium sulfate, and filtered, and the filtrate was concentrated to give the target product (26.7 g, yield 94%). [M−H]− 294.1

Step 3: 1-(2,2-diethoxyethyl)-5,5-dimethyl-1,4,5,6-tetrahydrocyclopenta[b]pyrrole-2-carboxamide At 0° C.-5° C., under nitrogen, to a solution of 1-(2,2-diethoxyethyl)-5,5-dimethyl-1,4,5,6-tetrahydrocyclopenta[b]pyrrole-2-carboxylic acid (26.7 g, 90.5 mmol) in DMF (150 mL) were added triethylamine (25 mL, 181 mmol) and then HATU (51.6 g, 136 mmol). After reacting at room temperature for 1 hour, the reaction solution was poured into concentrated aqueous ammonia (800 mL), stirred for 10 minutes, and extracted with dichloromethane (300 mL×2). The organic phase was collected and combined, and concentrated to give the target product (26.6 g, yield 100%), which was directly used in the next step.

Step 4: 7,7-dimethyl-7,8-dihydro-2H-cyclopenta[4,5]pyrrolo[1,2-a]pyrazin-1(6H)-one 1-(2,2-diethoxyethyl)-5,5-dimethyl-1,4,5,6-tetrahydrocyclopenta[b]pyrrole-2-carboxamide (26.6 g, 90.5 mmol) was dissolved in acetic acid (100 mL). The mixture was reacted at 100° C. for 4 hours (acetic acid was removed in vacuum under reduced pressure, and the pH value was adjusted to 8-9 with aqueous ammonia); water (200 mL) was added, and the mixture was extracted with dichloromethane (200 mL×3). The organic phase was collected and combined, and concentrated in vacuum under reduced pressure, and the resulting residue was purified with silica gel column chromatography (dichloromethane/methanol) to give the target product (18.3 g, yield 100%). [M+H]+ 203.1. 11H NMR (400 MHz, DMSO-d6) δ 10.21 (s, 1H), 6.98 (d, J=5.6 Hz, 1H), 6.58 (s, 1H), 6.48 (t, J=5.6 Hz, 1H), 2.62-2.60 (m, 2H), 2.47-2.46 (m, 2H), 1.19-1.17 (m, 6H).

Step 5: 4-chloro-2-(7,7-dimethyl-1-oxo-1,6,7,8-tetrahydro-2H-cyclopenta[4,5]pyrrolo[1,2-a]pyrazin-2-yl)nicotinaldehyde Under nitrogen, to a solution of 7,7-dimethyl-7,8-dihydro-2H-cyclopenta[4,5]pyrrolo[1,2-a]pyrazin-1(6H)-one (14.2 g, 70.2 mmol) and 2-bromo-4-chloronicotinaldehyde (30.9 g, 141 mmol) in 1,4-dioxane (500 mL) were added cuprous iodide (13.6 g, 70.2 mmol), 4,7-dimethoxy-1,10-phenanthroline (1.18 g, 49.2 mmol) and cesium carbonate (68.6 g, 211 mmol). The mixture was reacted at 80° C. for 16 hours, and then cooled to room temperature, and filtered; the filtrate was collected, and concentrated in vacuum under reduced pressure; and the resulting residue was recrystallized with ethanol to give the target product (13.8 g, yield 58%). [M+H]+ 342.1. 1H NMR (400 MHz, CDCl3) δ 10.21 (s, 1H), 8.53-8.43 (m, 1H), 7.40-7.31 (m, 1H), 7.10-7.02 (m, 1H), 6.95 (s, 1H), 6.89-6.81 (m, 1H), 2.68-2.54 (m, 4H), 1.27 (s, 6H).

Intermediate I-4

4-chloro-2-(10-fluoro-1-oxo-6,7,8,9-tetrahydropyrazino[1,2-a]indol-2(1H)-yl)nicotinaldehyde

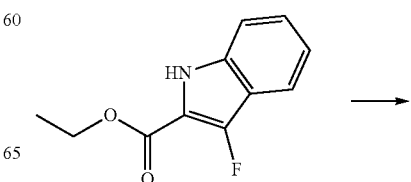

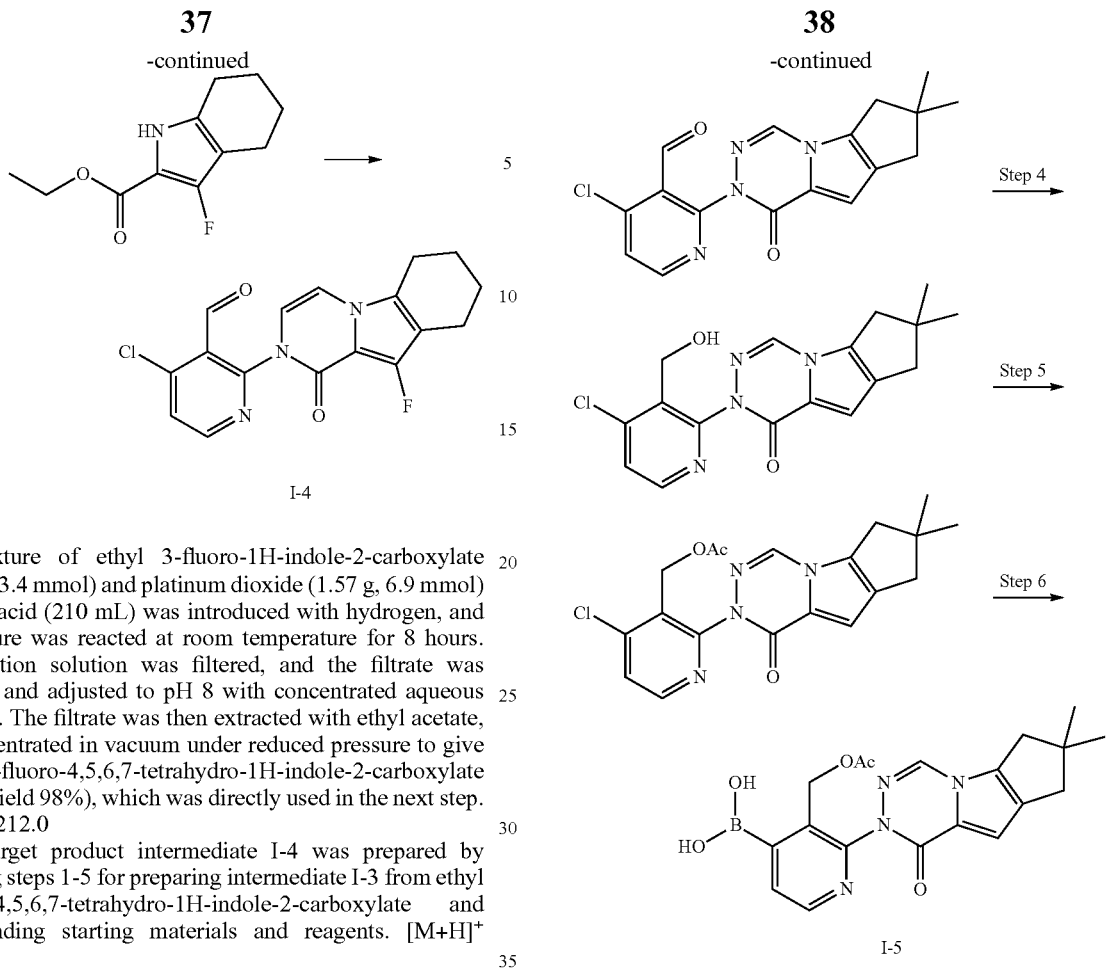

A mixture of ethyl 3-fluoro-1H-indole-2-carboxylate (10.5 g, 13.4 mmol) and platinum dioxide (1.57 g, 6.9 mmol) in acetic acid (210 mL) was introduced with hydrogen, and the mixture was reacted at room temperature for 8 hours. The reaction solution was filtered, and the filtrate was collected and adjusted to pH 8 with concentrated aqueous ammonia. The filtrate was then extracted with ethyl acetate, and concentrated in vacuum under reduced pressure to give ethyl 3-fluoro-4,5,6,7-tetrahydro-1H-indole-2-carboxylate (10.5 g, yield 98%), which was directly used in the next step. [M+H]$^+$ 212.0

The target product intermediate I-4 was prepared by following steps 1-5 for preparing intermediate I-3 from ethyl 3-fluoro-4,5,6,7-tetrahydro-1H-indole-2-carboxylate and corresponding starting materials and reagents. [M+H]$^+$ 346.1

Intermediate I-5

(3-(acetoxymethyl)-2-(7,7-dimethyl-1-oxo-1,6,7,8-tetrahydro-2H-cyclopenta[4,5]pyrrolo[1,2-d][1,2,4]triazin-2-yl)pyridin-4-yl)boronic acid

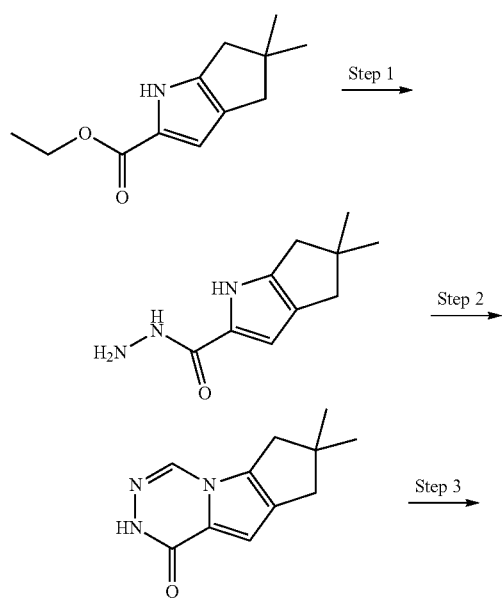

Step 1: 5,5-dimethyl-1,4,5,6-tetrahydrocyclopenta[b]pyrrole-2-carbohydrazide

To a solution of ethyl 5,5-dimethyl-1,4,5,6-tetrahydrocyclopenta[b]pyrrole-2-carboxylate (6.50 g, 31.4 mmol) in ethanol (15 mL) was added an aqueous hydrazine hydrate solution (45 mL, 36.0 mmol), and the mixture was reacted in a microwave reactor at 150° C. for 2 hours. The reaction solution was cooled to room temperature and filtered, and the filter cake was washed with water, collected, and dried in vacuum to give the target product (5.60 g, yield 92%), which was directly used in the next step. [M+H]$^+$ 194.1

Step 2: 7,7-dimethyl-7,8-dihydro-2H-cyclopenta[4,5]pyrrolo[1,2-d][1,2,4]triazin-1(6H)-one Under nitrogen, to a solution of 5,5-dimethyl-1,4,5,6-tetrahydrocyclopenta[b]pyrrole-2-carbohydrazide (5.60 g, 29.0 mmol) in DMF (16 mL) was added triethyl orthoformate (3.11 g, 21.0 mmol), and the mixture was reacted at 160° C. for 16 hours. The reaction solution was cooled to room temperature and filtered, and the filter cake was washed with a small amount of methanol, collected, and dried in vacuum to give the target product (3.25 g, yield 55%), which was directly used in the next step. [M+H]$^+$ 204.1

Step 3: 4-chloro-2-(7,7-dimethyl-1-oxo-1,6,7,8-tetrahydro-2H-cyclopenta[4,5]pyrrolo[1,2-d][1,2,4]triazin-2-yl)nicotinaldehyde Under nitrogen, to a solution of 7,7-dimethyl-7,8-dihydro-2H-cyclopenta[4,5]pyrrolo[1,2-d][1,2,4]triazin-1

(6H)-one (3.25 g, 16.0 mmol) and 2-bromo-4-chloronicotinaldehyde in 1,4-dioxane (60 mL) were added cuprous iodide (1.52 g, 8.0 mmol), 4,7-dimethoxy-1,10-phenanthroline (1.35 g, 5.6 mmol) and cesium carbonate (10.4 g, 32.0 mmol). The mixture was reacted at 80° C. for 4 hours, and then cooled to room temperature. The reaction solution was concentrated in vacuum under reduced pressure, and the resulting residue was purified with silica gel column chromatography to give the target product (3.43 g, yield 63%). [M+H]+ 343.1

Step 4: 2-(4-chloro-3-(hydroxymethyl)pyridin-2-yl)-7,7-dimethyl-7,8-dihydro-2H-cyclopenta[4,5]pyrrolo[1,2-d][1,2,4]triazin-1(6H)-one At 0° C.-5° C., under nitrogen, to a solution of 4-chloro-2-(7,7-dimethyl-1-oxo-1,6,7,8-tetrahydro-2H-cyclopenta[4,5] pyrrolo[1,2-d][1,2,4]triazin-2-yl)nicotinaldehyde (3.43 g, 10.0 mmol) in methanol (10 mL) and dichloromethane (30 mL) was added sodium borohydride (0.19 g, 5.0 mmol), and the mixture was reacted at this temperature for 10 minutes. A saturated aqueous ammonium chloride solution (10 mL) was added to the reaction solution, and the mixture was extracted with dichloromethane (80 mL×2). The organic phase was collected and combined, and concentrated in vacuum under reduced pressure to give the target product (3.33 g, yield 97%), which was directly used in the next step. [M+H]+ 345.1

Step 5: (4-chloro-2-(7,7-dimethyl-1-oxo-1,6,7,8-tetrahydro-2H-cyclopenta[4,5]pyrrolo[1,2-d][1,2,4]triazin-2-yl)pyridin-3-yl)methyl acetate At 0° C.-5° C., under nitrogen, to a solution of 2-(4-chloro-3-(hydroxymethyl)pyridin-2-yl)-7,7-dimethyl-7,8-dihydro-2H-cyclopenta[4,5]pyrrolo[1,2-d][1,2,4]triazin-1(6H)-one (3.33 g, 9.7 mmol) and triethylamine (3.91 g, 38.6 mmol) in dichloromethane (60 mL) was added acetylchloride (11.4 g, 145 mmol), and the mixture was reacted at this temperature for 1 hour. Water (30 mL) and dichloromethane (80 mL) were added to the reaction solution; the organic phase was collected and combined, and concentrated in vacuum under reduced pressure; and the resulting residue was purified with silica gel column chromatography (petroleum ether/ethyl acetate) to give the target product (2.84 g, yield 76%). [M+H]+ 387.1

Step 6: (3-(acetoxymethyl)-2-(7,7-dimethyl-1-oxo-1,6,7,8-tetrahydro-2H-cyclopenta[4,5]pyrrolo[1,2-d][1,2,4]triazin-2-yl)pyridin-4-yl)boronic acid Under nitrogen, to a solution of (4-chloro-2-(7,7-dimethyl-1-oxo-1,6,7,8-tetrahydro-2H-cyclopenta[4,5]pyrrolo[1,2-d][1,2,4]triazin-2-yl)pyridin-3-yl)methyl acetate (2.84 g, 7.3 mmol) and bis(pinacolato)diboron (5.59 g, 22.0 mmol) in 1,4-dioxane (200 mL) were added Xphos (0.35 g, 0.73 mmol), Pd(dppf)Cl$_2$ CH$_2$Cl$_2$ (0.60 g, 0.73 mmol) and potassium acetate (2.16 g, 22.0 mmol). The mixture was reacted at 100° C. for 16 hours, and then cooled to room temperature. The reaction solution was concentrated in vacuum under reduced pressure, and the resulting residue was purified with silica gel column chromatography (petroleum ether/ethyl acetate) to give the target product (2.55 g, yield 88%). [M+H]+ 397.1

The intermediates in the table below were prepared by following steps 4-6 for preparing intermediate I-5 from intermediate I-3 and corresponding starting materials and reagents:

| Intermediates | Structural formula | LC-MS [M + H]+ |
|---|---|---|
| I-7 | 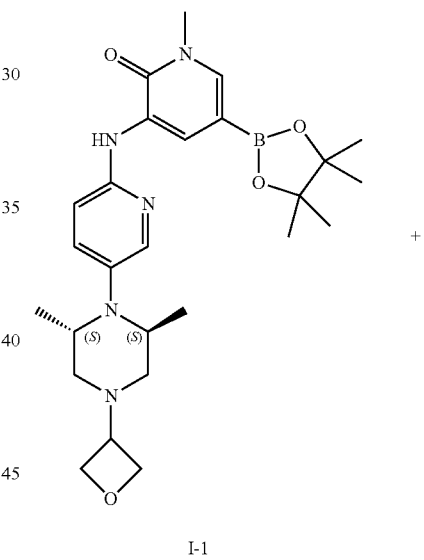 | 396.1 |

Compound 1

2-(5-((5-((2S,6S)-2,6-dimethyl-4-(oxetan-3-yl)piperazin-1-yl)pyridin-2-yl)amino)-3'-(hydroxymethyl)-1-methyl-6-oxo-1,6-dihydro-[3,4'-bipyridin]-2'-yl)-7,7-dimethyl-7,8-dihydro-2H-cyclopenta[4,5]pyrrolo[1,2-a]pyrazin-1(6H)-one

I-1

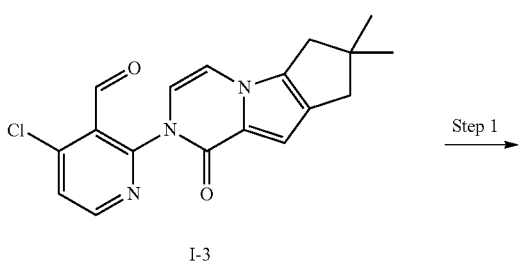

I-3

Step 1 →

-continued

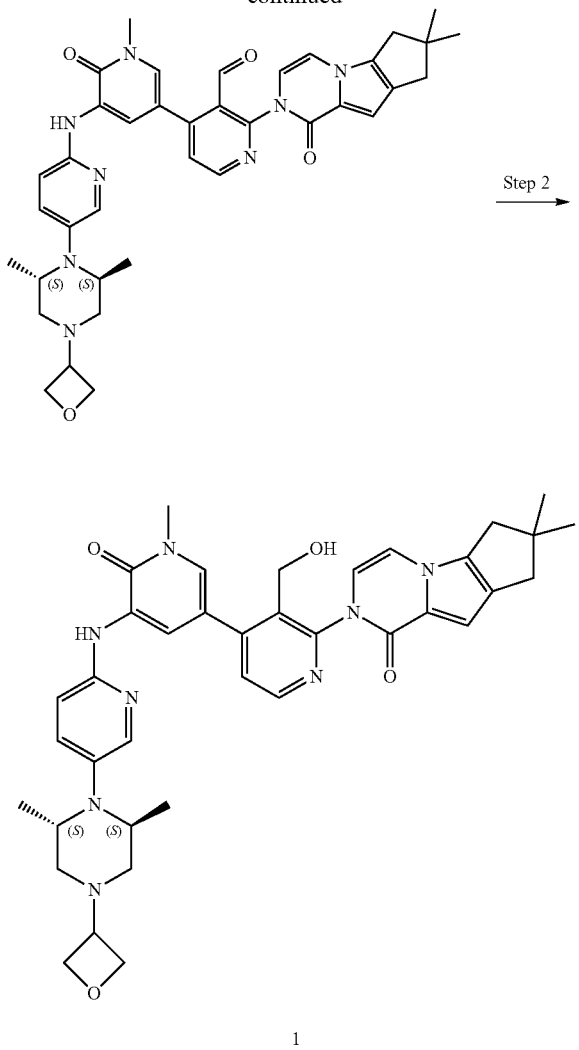

1

Step 1: 2'-(7,7-dimethyl-1-oxo-1,6,7,8-tetrahydro-2H-cyclopenta[4,5]pyrrolo[1,2-a]pyrazin-2-yl)-5-((5-((2S,6S)-2,6-dimethyl-4-(oxetan-3-yl)piperazin-1-yl)pyridin-2-yl)amino)-1-methyl-6-oxo-1,6-dihydro-[3,4'-bipyridine]-3'-carbaldehyde Under nitrogen, to a solution of intermediate I-1 (99 mg, 0.20 mmol) and intermediate I-3 (68 mg, 0.20 mmol) in 1,4-dioxane (3 mL) and water (0.2 mL) were added Xphos (9 mg, 0.02 mmol), Pd(dppf)Cl$_2$·CH$_2$Cl$_2$ (16 mg, 0.02 mmol) and cesium carbonate (130 mg, 0.40 mmol). The mixture was reacted at 90° C. for 2 hours, and then cooled to room temperature. The reaction solution was filtered, and the filtrate was collected and concentrated in vacuum under reduced pressure to give the target product, which was directly used in the next step. [M+H]$^+$ 675.3

Step 2: 2-(5-((5-((2S,6S)-2,6-dimethyl-4-(oxetan-3-yl)piperazin-1-yl)pyridin-2-yl)amino)-3'-(hydroxymethyl)-1-methyl-6-oxo-1,6-dihydro-[3,4'-bipyridin]-2'-yl)-7,7-dimethyl-7,8-dihydro-2H-cyclopenta[4,5]pyrrolo[1,2-a]pyrazin-1(6H)-one At 0° C.-5° C., under nitrogen, to a solution of 2'-(7,7-dimethyl-1-oxo-1,6,7,8-tetrahydro-2H-cyclopenta[4,5] pyrrolo[1,2-a]pyrazin-2-yl)-5-((5-((2S,6S)-2,6-dimethyl-4-(oxetan-3-yl)piperazin-1-yl)pyridin-2-yl)amino)-1-methyl-6-oxo-1,6-dihydro-[3,4'-bipyridin]-3'-carbaldehyde obtained from step 1 in methanol (0.5 mL) and dichloromethane (5 mL) was added sodium borohydride (7 mg, 0.20 mmol), and the mixture was reacted at room temperature for 5 minutes. The reaction solution was added with water (0.5 mL), and concentrated in vacuum under reduced pressure, and the resulting residue was purified with silica gel column chromatography (methanol/water) and thin layer chromatography (methanol/dichloromethane=1/20) to give the target product (74 mg, yield 55%). [M+H]$^+$ 677.4. $^1$H NMR (400 MHZ, CD3OD): δ8.74-8.69 (m, 1H), 8.56-8.51 (m, 1H), 7.95-7.91 (m, 1H), 7.60-7.57 (m, 1H), 7.54-7.51 (m, 1H), 7.40-7.36 (m, 1H), 7.23-7.19 (m, 1H), 7.03-7.00 (m, 1H), 6.95-6.90 (m, 1H), 6.80-6.75 (m, 1H), 4.70-4.65 (m, 2H), 4.64-4.57 (m, 2H), 4.56-4.52 (m, 1H), 4.50-4.45 (m, 1H), 3.69 (s, 3H), 3.54-3.46 (m, 2H), 3.46-3.39 (m, 1H), 2.78-2.68 (m, 2H), 2.65-2.58 (m, 2H), 2.57-2.52 (m, 2H), 2.22-2.13 (m, 2H), 1.30-1.26 (m, 6H), 0.98-0.94 (m, 6H).

The compounds in the table below were prepared by following the steps for preparing compound 1 from corresponding intermediates and reagents:

| Compounds | Structural formula | LC-MS [M + H]$^+$ | $^1$H NMR | Intermediates |
|---|---|---|---|---|
| 2 | | 677.4 | $^1$H NMR (400 MHz, CD$_3$OD) δ 8.83-8.75 (m, 1H), 8.58-8.53 (m, 1H), 8.03-7.94 (m, 1H), 7.63-7.58 (m, 1H), 7.58-7.52 (m, 2H), 7.26-7.19 (m, 1H), 7.11-7.04 (m, 1H), 6.93 (s, 1H), 6.82-6.76 (m, 1H), 4.73-4.68 (m, 2H), 4.65-4.58 (m, 3H), 4.52-4.45 (m, 1H), 3.71 (s, 3H), 3.54-3.46 (m, 1H), 3.16-3.07 (m, 2H), 2.83-2.77 (m, 2H), 2.77-2.69 (m, 2H), 2.66-2.57 (m, 2H), 1.94-1.71 (m, 2H), 1.30-1.27 (m, 6H), 0.79-0.71 (m, 6H). | I-2 I-3 |

-continued

| Compounds | Structural formula | LC-MS [M + H]+ | 1H NMR | Intermediates |
|---|---|---|---|---|
| 3 | 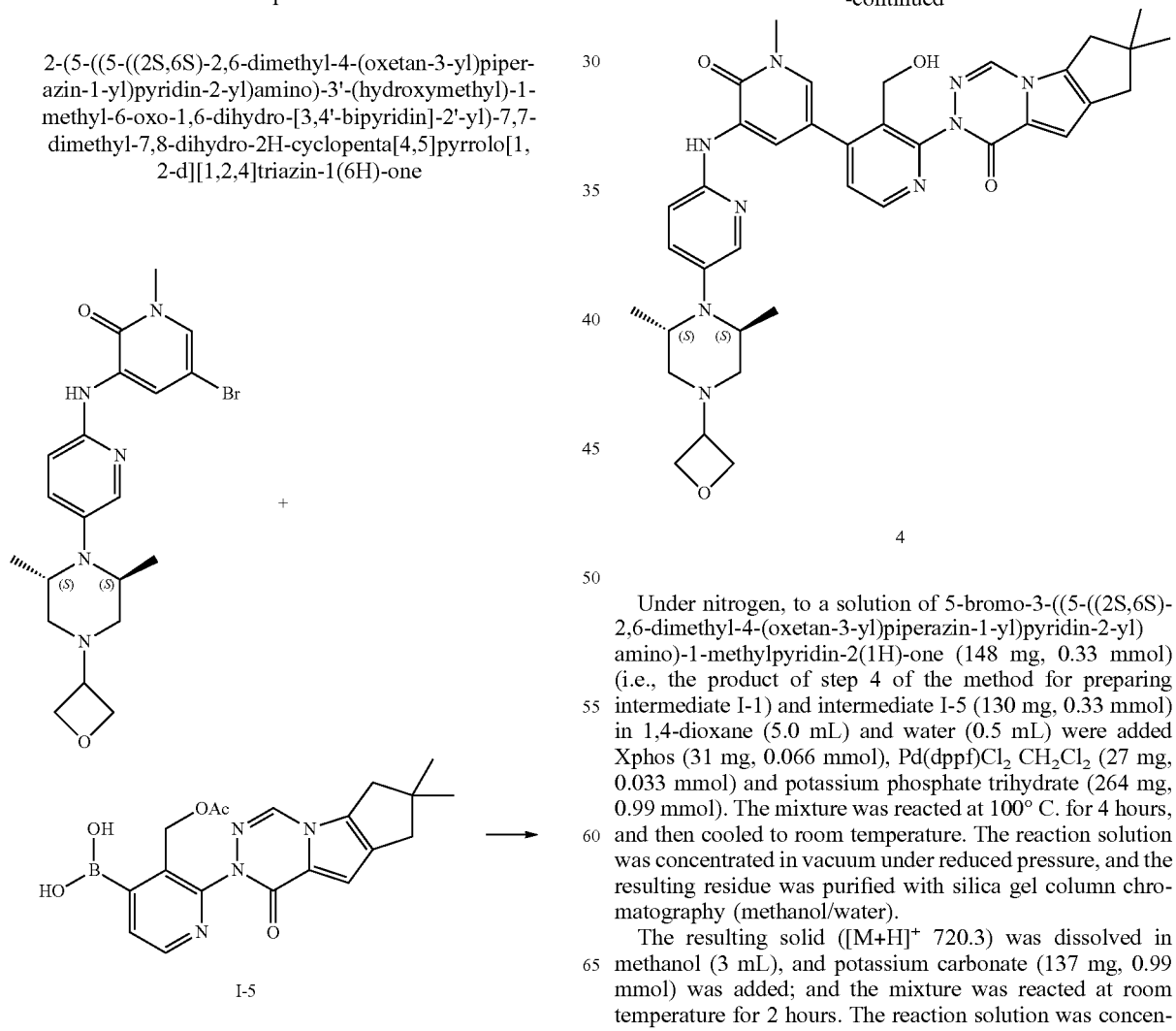 | 681.3 | 1H NMR (400 MHz, CD3OD) δ 8.72-8.70 (m, 1H), 8.55-8.52 (m, 1H), 7.93 (d, J = 7.6 Hz, 1H), 7.58 (d, J = 5.1 Hz, 1H), 7.53-7.51 (m, 1H), 7.41-7.37 (m, 1H), 7.15 (d, J = 6.0 Hz, 1H), 7.02 (d, J = 8.8 Hz, 1H), 6.70 (d, J = 6.0 Hz, 1H), 4.72-4.50 (m, 6H), 3.70 (s, 3H), 3.55-3.39 (m, 3H), 2.75-2.71 (m, 2H), 2.65-2.49 (m, 4H), 2.20-2.16 (m, 2H), 1.97-1.78 (m, 4H), 0.99-0.95 (m, 6H). | I-1 I-4 |

Compound 4

2-(5-((5-((2S,6S)-2,6-dimethyl-4-(oxetan-3-yl)piperazin-1-yl)pyridin-2-yl)amino)-3'-(hydroxymethyl)-1-methyl-6-oxo-1,6-dihydro-[3,4'-bipyridin]-2'-yl)-7,7-dimethyl-7,8-dihydro-2H-cyclopenta[4,5]pyrrolo[1,2-d][1,2,4]triazin-1(6H)-one Under nitrogen, to a solution of 5-bromo-3-((5-((2S,6S)-2,6-dimethyl-4-(oxetan-3-yl)piperazin-1-yl)pyridin-2-yl)amino)-1-methylpyridin-2(1H)-one (148 mg, 0.33 mmol) (i.e., the product of step 4 of the method for preparing intermediate I-1) and intermediate I-5 (130 mg, 0.33 mmol) in 1,4-dioxane (5.0 mL) and water (0.5 mL) were added Xphos (31 mg, 0.066 mmol), Pd(dppf)Cl2·CH2Cl2 (27 mg, 0.033 mmol) and potassium phosphate trihydrate (264 mg, 0.99 mmol). The mixture was reacted at 100° C. for 4 hours, and then cooled to room temperature. The reaction solution was concentrated in vacuum under reduced pressure, and the resulting residue was purified with silica gel column chromatography (methanol/water).

The resulting solid ([M+H]+ 720.3) was dissolved in methanol (3 mL), and potassium carbonate (137 mg, 0.99 mmol) was added; and the mixture was reacted at room temperature for 2 hours. The reaction solution was concentrated in vacuum under reduced pressure, and the resulting residue was purified with silica gel column chromatography (methanol/water) and thin layer chromatography (methanol/dichloromethane=1/20) to give the target product (30 mg, yield 13%). [M+H]$^+$ 678.3. $^1$H NMR (400 MHz, CD$_3$OD): δ8.72-8.86 (m, 1H), 8.58-8.52 (m, 1H), 8.43-8.38 (m, 1H), 7.97-7.92 (m, 1H), 7.63-7.58 (m, 1H), 7.53-7.48 (m, 1H), 7.42-7.36 (m, 1H), 7.08-6.99 (m, 2H), 4.70-4.52 (m, 6H), 3.70 (s, 3H), 3.55-3.41 (m, 3H), 2.87-280 (m, 2H), 2.67-2.61 (m, 2H), 2.60-2.51 (m, 2H), 2.24-2.12 (m, 2H), 1.32-1.29 (m, 6H), 1.00-0.94 (m, 6H).

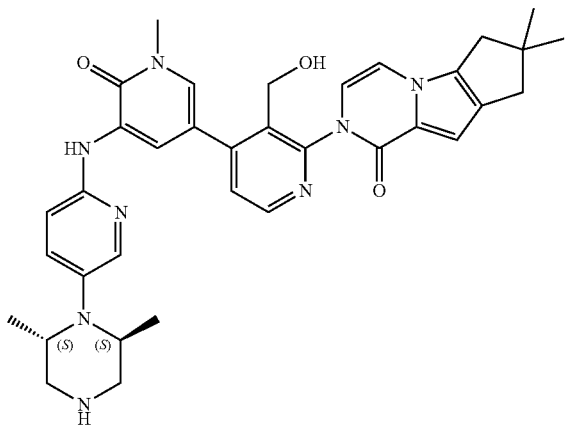

5

The compounds in the table below were prepared by following the steps for preparing compound 4 from corresponding intermediates and reagents:

| Compounds | Structural formula | LC-MS [M + H]$^+$ | Intermediates |
|---|---|---|---|
| 5a | | 721.2 | I-6<br>I-7 |

Compound 5
2-(5-(((5-((2S,6S)-2,6-dimethylpiperazin-1-yl)pyridin-2-yl)amino)-3'-(hydroxymethyl)-1-methyl-6-oxo-1,6-dihydro-[3,4'-bipyridin]-2'-yl)-7,7-dimethyl-7,8-dihydro-2H-cyclopenta[4,5]pyrrolo[1,2-a]pyrazin-1(6H)-one

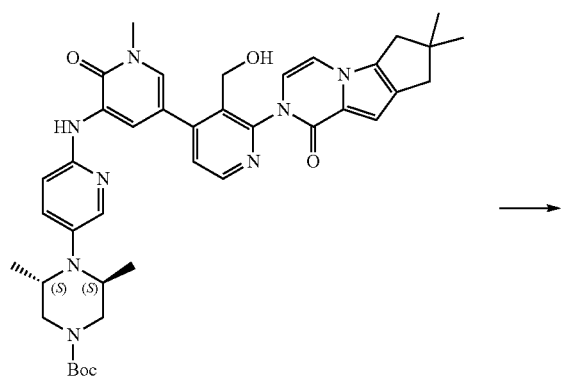

5a

Compound 5a (500 mg, 0.69 mmol) was dissolved in trifluoroacetic acid (5 mL), and the mixture was stirred at room temperature for 30 minutes. The mixture was concentrated in vacuum under reduced pressure, and the resulting residue was dissolved in methanol (5 mL) and triethylamine (1 mL) was added. The mixture was concentrated in vacuum under reduced pressure again. The resulting residue was purified with silica gel column chromatography (methanol/water) to give the target product (340 mg, yield 79%). [M+H]$^+$ 621.4. 11H NMR (400 MHz, CD$_3$OD) δ8.78 (s, 1H), 8.60-8.51 (m, 1H), 8.00 (s, 1H), 7.61-7.56 (m, 1H), 7.56-7.51 (m, 1H), 7.48-7.38 (m, 1H), 7.27-7.18 (m, 1H), 7.09-7.01 (m, 1H), 6.93 (s, 1H), 6.81-6.75 (m, 1H), 4.64-4.58 (m, 1H), 4.53-4.46 (m, 1H), 3.70 (s, 3H), 3.69-3.61 (m, 2H), 3.44-3.37 (m, 2H), 3.11-3.02 (m, 2H), 2.79-2.68 (m, 2H), 2.66-2.56 (m, 2H), 1.30-1.26 (m, 6H), 1.09-0.99 (m, 6H).

Compound 6

2-(3'-(hydroxymethyl)-1-methyl-6-oxo-5-((5-((2S,6S)-2,4,6-trimethylpiperazin-1-yl)pyridin-2-yl)amino)-1,6-dihydro-[3,4'-bipyridin]-2'-yl)-7,7-dimethyl-7,8-dihydro-2H-cyclopenta[4,5]pyrrolo[1,2-a]pyrazin-1(6H)-one

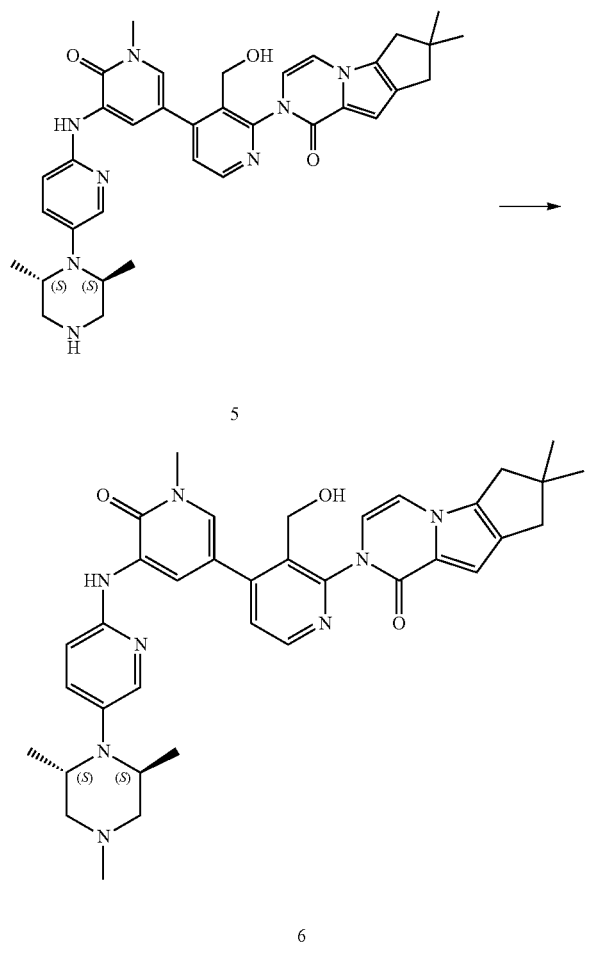

To a solution of compound 5 (200 mg, 0.32 mmol) in methanol (5 mL) was added an aqueous formaldehyde solution (1.2 mL), and the mixture was stirred at room temperature for 5 minutes. Sodium borohydride (38 mg, 1.0 mmol) was added, and the mixture was stirred at room temperature for 30 minutes. The reaction solution was purified with silica gel column chromatography (methanol/water) to give the target product (78 mg, yield 38%). [M+H]$^+$ 635.3. $^1$H NMR (400 MHz, CD$_3$OD) δ8.74-8.69 (m, 1H), 8.58-8.51 (m, 1H), 7.97-7.90 (m, 1H), 7.62-7.56 (m, 1H), 7.55-7.50 (m, 1H), 7.41-7.34 (m, 1H), 7.25-7.19 (m, 1H), 7.05-6.99 (m, 1H), 6.93 (s, 1H), 6.81-6.75 (m, 1H), 4.62-4.58 (m, 1H), 4.51-4.46 (m, 1H), 3.70 (s, 3H), 3.53-3.46 (m, 2H), 2.78-2.69 (m, 2H), 2.69-2.58 (m, 4H), 2.36-2.18 (m, 5H), 1.29-1.27 (m, 6H), 0.98-0.90 (m, 6H).

Example 2 Determination of Biochemical BTK

1. Reagents and Materials
   BTK recombinant protein: Invitrogen, Cat #PV3363;
   Z'-LYTE® kinase test kit-tyrosine 1 peptide: Invitrogen, Cat #PV3190;
   384-well low-flange black flat-bottomed polystyrene NBS microplate, no lid, no sterilization: Corning, Cat #3575;
   96-well polystyrene conical-bottomed MicroWell™ plate, sealed with a lid: Thermo Scientific™ Nunc™, Cat #277143;
   Envision multi-mode plate reader: PerkinElmer;
   Mixmate® shaker: Eppendorf;
   TS-2102 shaking incubator: TENSUC;
2. Methods
   Z'-LYTE® biochemical assay employs a fluorescence resonance energy transfer (FRET)-based, coupled-enzyme format and is based on the differential sensitivity of phosphorylated and non-phosphorylated peptides to proteolytic cleavage. Both ends of the short peptide substrate are labeled with two fluorescent groups to form a FRET paired combination. In the primary reaction (the Kinase Reaction), the kinase transfers the γ-phosphate of ATP to a single serine or threonine residue on the short peptide substrate. In the secondary reaction (the development reaction), the non-phosphorylated short peptides were recognized and cleaved by a site-specific protease (the development reagent). Phosphorylated short peptides can resist such cleavage. Cleavage of short peptides can disrupt the donor (such as coumarin) and receptor fluorophores (fluorescein) on the short peptides, while the phosphorylated short peptides can maintain FRET. The calculation method of the ratio is as follows, and the ratio of the respective emission signals generated by the donor fluorophores emitted (after excitation at 400 nm) to the receptors is calculated. Emission signal ratio=emitted light by coumarin (445 nm)/emitted light by fluorescein (520 nm). If the FRET short peptide is phosphorylated (such as no kinase inhibitor), the emitted light ratio will remain in a lower level. If the FRET short peptide is non-phosphorylated (such as kinase inhibitor), the emitted light ratio will be in a higher level. In this way, the inhibitory effects of different compound inhibitors on BTK kinase activity would be distinguished.

The experiment was carried out according to the instructions of the Z'-LYTE® kinase test kit-tyrosine 1 peptide. Reagent preparation: 1.33×kinase buffer: 5×kinase buffer was diluted with water to 1.33×kinase buffer; an enzyme solution: the kinase was dissolved in 1.33×kinase buffer with the final working concentration being 3.32 nM; a short peptide solution: a short peptide stock solution (1 mM dissolved in DMSO) was dissolved in 1.33×kinase buffer with the final working concentration being 2 μM; Z'-LYTE Tyr01 phosphorylated short peptide solution, 0.6 μl of stock solution (1 mM dissolved in DMSO) was dissolved in 149.4 μl of 1.33×kinase buffer; an ATP solution: an ATP stock solution (10 mM aqueous solution) was dissolved in 1.33× kinase buffer with the final working concentration being 32 μM; a color-developing solution: color-developing solution B was dissolved in color-developing buffer with the final working concentration being 1×color-developing solution; 4×compound preparation: the compound was diluted in 3-fold gradient concentration to finally obtain 4% DMSO aqueous solution containing different concentrations of the compound, with the final working concentration being 3000, 1000, 333.33, 111.11, 37.04, 12.35, 4.12, 1.37 nM, 8 concentration points in total.

Specific steps of the experiment: In the experiment, there were three control groups, each with 8 replicate wells, which were C1 100% inhibition group (no ATP), C2 0% inhibition group (with ATP), and C3 100% phosphorylation group, respectively. 2.5 μl of serially diluted compound was added to each well of a 384-well plate, with double replicate wells, and 4% DMSO solution was added to wells C1, C2, and C3. After that, except for wells C3, 2.5 μl of BTK enzyme solution was added to each remaining well, which was left to stand at 4° C. for 30 minutes. After that, except for wells C3, 2.5 μl of short peptide solution was added to each well, and 5 μl of phosphorylated short peptide solution was added to each of wells C3. 2.5 μl of 1.33×kinase buffer was added to each of wells C1 and C3, and 2.5 μl of ATP solution was added to each of the remaining wells. The wells were centrifuged transiently, and the plate was shaken at 1000 rpm for 30 seconds to perform transient centrifuge. The 384-well plate was placed in a shaking incubator protected from light and incubated at room temperature for 1 hour. After the enzymatic reaction was completed, 5 μl of development solution was added to each well, which was centrifuged transiently, and the plate was shaken at 1000 rpm for 30 seconds to perform transient centrifuge. The 384-well plate was placed in a shaking incubator protected from light and incubated at room temperature for 1 hour until the color-developing reaction was completed.

3. Detection

After the development reaction was completed, the 384-well plate was taken out to perform plate reading using the Envision multi-mode plate reader, and the optical signal was detected at the emission wavelength of 405 nm and the excitation wavelength of 460 nm/535 nm. The reading value at 460 nm/535 nm of each well was used as the signal value of each well.

4. Calculation

The average signal value of C3 was regarded as 100% phosphorylation, the average signal value of C1 was regarded as 0% phosphorylation, and the average signal value of C2 was used to calculate the phosphorylation ratio of short peptides in the presence of BTK kinase. According to the signal value in each well, the inhibition ratio (%) of each concentration of compounds was calculated, and the 205 model in XL-Fit 5.3 software (ID Business Solutions Limited) was used to obtain an $IC_{50}$ value.

The Phosphorylation Ratio is Calculated as Follows:

Phosphorylation ratio (%)=100−100×[(emission signal ratio×$F_{100\%}$−$C_{100\%}$]/{($C_{0\%}$−$C_{100\%}$)+[emission signal ratio×($F_{100\%}$−$F_{0\%}$)]} wherein, the emission signal ratio=coumarin emission signal (460 nm)/fluorescein emission signal (535 nm); $C_{100\%}$=average value of coumarin emission signal in C3; $C_{0\%}$=average value of coumarin emission signal in C1; $F_{100\%}$=average value of fluorescein emission signal in C3; $F_{0\%}$=average value of fluorescein emission signal in C1.

The Inhibition Ratio is Calculated as Follows:

Inhibition ratio (%)=100×(phosphorylation ratio in C2−phosphorylation ratio in testing well)/phosphorylation ratio in C2

5. Test results

| Compound No. | $IC_{50}$ (μM) |
|---|---|
| 1 | 0.010 |
| 2 | 0.007 |
| 3 | 0.003 |
| 4 | 0.005 |
| 5 | 0.008 |
| 6 | 0.007 |

Example 3

Determination of Phosphorylated BTK in Ramos Cells

1. Reagents and Materials

Ramos cells: Ramos cells were purchased from American Standard Biological Collection Center ATCC Cell Bank, PRMI 1640 medium containing L-glutamine, 1.5 g/L of sodium bicarbonate, 2.383 g/L of HEPES solution, 0.11 g/L of sodium pyruvate and 4.5 g/L of glucose was used, added 10% fetal bovine serum FBS, and placed in a 5% $CO_2$, 37° C. cell incubator for normal culture;

PRMI 1640 medium: GIBCO, Cat #A10491-01;
Fetal bovine serum (FBS): GIBCO, Cat #100100-147;
Hank's balanced salt solution (HBSS): GIBCO, Cat #14025-092;
Immunoglobulin M (IgM): Jackson Immuno, Cat #109-006-129;
3% hydrogen peroxide (3% $H_2O_2$): Sigma, Cat #88597-100ML-F;
Phosphorylated BTK HTRF detection kit (BTK phospho-Y223 HTRF kit): Cisbio, Cat #63ADK017PEH;
Microwell plate reader: Envision, Perkin Elmer;
384-well plate CulturPlateTM384: Perkin Elmer, Cat #6007680
96-well plate: Corning, Cat #3799.

2. Methods

Ramos cells were starved in PRMI 1640 medium with 1% FBS for 2 hours. The starved Ramos cells were diluted with Hank's balanced salt solution to 5.0×10⁶ cells/ml, seeded in a 96-well plate with 20 μL/well (1.0×10⁵ cells/well), and cultured in a 5% $CO_2$, 37° C. cell incubator. After culturing for 1 hour, the test compound was diluted with Hank's balanced salt solution in 4-fold gradient to the corresponding concentrations, and then 5 μL/well of the diluted test compound with different concentrations (the final concentrations of the test compound were 3.0, 0.75, 0.188, 0.047, 0.012, 0.0029, 0.0007 and 0.00018 μM, and the final concentration of DMSO was 0.3%, double replicate wells) or 5 μL/well of control solution (1.5% DMSO, 8 replicate wells) were added to 20 μL/well of cell culture system, which incubated together for another hour, then 5 μL/well of a mixed solution of human immunoglobulin M (final concentration was 10 μg/mL) and hydrogen peroxide (final concentration was 3.3 mM) diluted with Hank's balanced salt solution was added to the treating wells for the test compound and the control treating wells for anti-human immunoglobulin M, and 5 μL/well of Hank's balanced salt solution was added to negative control treating wells. The plate was incubated in a 5% $CO_2$, 37° C. cell incubator for 10 minutes.

10 μL/well of cell lysis buffer was added to each well of a 96-well plate, which was mixed well and lysed at room temperature for 30 minutes. 16 μL/well of lysis buffer was pipetted to a new 384 well plate, and then added 4 μL/well of phosphorylated BTK antibody, centrifuged (1000 rpm)

for 1 minute, then shaken for 1 minute, further centrifuged (1000 rpm) for 1 minute, and finally placed in a constant temperature incubator overnight. Detection was performed on the next day.

3. Detection

The 384 well plate incubated overnight in the constant temperature incubator was taken out to detect the luminescence signal using the Envision microwell plate reader at the emission wavelength of 320 nm and excitation wavelength of 665 nm/615 nm. The reading value at 665 nm/615 nm of each well multiplied by 104 was used as the signal value of each well.

4. Calculation

The average signal value of the wells supplemented with the mixed solution of human immunoglobulin M (final concentration was 10 μg/mL) and hydrogen peroxide (final concentration was 3.3 mM) without the test compound was regarded as the high value, and the average signal value of the wells without immunoglobulin M stimulation and without the test compound was regarded as the low value. According to the signal value in each well, the inhibition ratio (%) of each concentration of compounds was calculated, and the 205 model in XL-Fit 5.3 software (ID Business Solutions Limited) was used to obtain an $IC_{50}$ value. The Inhibition Ratio is Calculated as Follows:

inhibition ratio (%)=100%−{(treating well for the test compound−negative control treating well)/ (control treating well for anti-human immunoglobulin M−negative control treating well)}× 100%, wherein, Treating well for the test compound: represents the signal value of Ramos cells treated with anti-human immunoglobulin M, hydrogen peroxide and the test compound.

Control treating well for anti-human immunoglobulin M: represents the signal value of Ramos cells treated with anti-human immunoglobulin M, hydrogen peroxide but without the test compound.

Negative control treating well: represents the signal value of Ramos cells without the test compound and without immunoglobulin stimulation.

5. Test Results

| Compound No. | $IC_{50}$ (μM) |
| --- | --- |
| 1 | 0.005 |
| 2 | 0.006 |
| 3 | 0.003 |
| 4 | 0.003 |
| 5 | 0.008 |
| 6 | 0.007 |

Example 4 Determination of B Cell Activity in Whole Blood of Rats

1. Reagents and Materials

Peripheral whole blood of female Wistar rats;
phosphate buffer PBS: GIBCO, Cat #C20012500BT;
anti-rat B220PE antibody (PE anti-rat B220): eBioscience, Cat #12-0460-82;
anti-rat CD86 FITC antibody (FITC anti-rat CD86): eBioscience, Cat #11-0860-82;
10 times lysis buffer (10×lysis buffer): BD Biosciences, Cat #555899;
fixation buffer (IC fixation buffer): Invitrogen, Cat #00-8222-49;
96 well U-shaped bottom plate: Nunc, Cat #163320;
96 well V-shaped bottom plate: Nunc, Cat #49952;
dimethyl sulfoxide (DMSO): Sigma-Aldrich, Cat #34869-4L;
anti-rat immunoglobulin D (Mouse Anti-rat IgD): Biorad, Cat #MCA190;
flow cytometer: BD FACS Canto II, BD.

2. Methods

In the determination of the compound activity, the collected peripheral whole blood of rat was added to a 96 well plate at 80 μL/well and cultured in a 5% $CO_2$, 37° C. cell incubator. After half an hour, the test compound was diluted with PBS in a 3-fold gradient to the corresponding concentrations, and then the diluted test compound with different concentrations was added to the culture system of rat whole blood at 10 μL/well (the final concentration of the test compound was 1.0, 0.33, 0.11, 0.037, 0.012, 0.0041, 0.0014, and 0.0005 μM, the final concentration of DMSO was 0.3%, double replicate wells), or the control solution (0.3% DMSO, 6 replicate wells) was added to the corresponding well at 10 μL/well, which were incubated in the cell incubator for one hour. Then 10 μL/well of anti-rat immunoglobulin D diluted in PBS (the final concentration was 10 μg/mL) was add to the treating wells of the test compound and control wells for anti-rat immunoglobulin D, or 10 μL/well of PBS was added to the negative control wells, which were mixed well to continue the culture in a 5% $CO_2$, 37° C. cell incubator, and incubated for 18 hours.

On the second day, the 96-well plates were taken out and the flow cytometry antibody mixture (the final concentration of anti-rat B220PE antibody was 1 μg/mL and the final concentration of anti-rat CD86 FITC antibody was 1 μg/mL) diluted with PBS was added to each well of plate, which were incubated for 30 minutes in the dark, and then 50 μL of blood from each well was pipetted to the freshly prepared 500 μL of lysis buffer to lyse red blood cells. The plates were shaken for 20 minutes, centrifuged to remove the supernatant, then washed, fixed, and detected on a flow cytometer.

3. Detection

The B cell activation in the sample was determined by flow dyeing method.

4. Calculation

The average value of the proportion of activated B cells in the wells with anti-rat immunoglobulin D but without the test compound was used as the control treating well for anti-rat immunoglobulin D, and the average value of the proportion of activated B cells in the wells without immunoglobulin D stimulation and without the test compound was used as the negative control treating well. According to the B cell activation ratio in each well, the inhibition ratio (%) of each concentration was calculated, and then the $IC_{50}$ value was obtained by using the 205 model in XL-Fit 5.3 software (ID Business Solutions Limited).

The Inhibition Ratio is Calculated as Follows:

inhibition ratio (%)=100%−{(treating well for the test compound−negative control treating well)/ (control treating well for anti-rat immunoglobulin D−negative control treating well)}×100%, wherein, Treating well for the test compound: represents the B cell activation ratio in rat whole blood treated with anti-rat immunoglobulin D and the test compound.

Control treating well for anti-rat immunoglobulin D: represents the B cell activation ratio in rat whole blood treated with anti-rat immunoglobulin D but without the test compound.

Negative control treating well: represents the B cell activation ratio in rat whole blood without the test compound and without immunoglobulin stimulation.

Through the above-mentioned test, the compounds of the present invention showed good potency in inhibiting B cell activation in rat whole blood. The $IC_{50}$ value of compound 1 is 0.001 µM.

Example 5 Stability Test in Liver Microsomes

1. Experiment Materials:

Both male CD-1 mouse pooled liver microsomes and male SD rat pooled liver microsomes were purchased from BioreclamationIVT Corporation, USA.

Phenacetin, glucose-6-phosphate dehydrogenase (G-6-PDH) and nicotinamide adenine dinucleotide phosphate (NADP) were all purchased from Sigma-Aldrich Corporation, USA. Glucose-6-phosphate (G-6-P) was purchased from Shanghai Eybridge Chemical Technology Co., Ltd. and Carbosynth China Limit.

2. Solution Preparation:

10 mM test compound stock solution: a certain amount of test compound was weighed, and dissolved with an appropriate volume of DMSO to prepare a stock solution with a concentration of 10 mM for use.

Reaction stopping solution: an appropriate amount of internal standard compound phenacetin was dissolved in acetonitrile to prepare a reaction stopping solution with a concentration of 1000 ng/mL for use at room temperature.

3. Experiment Method:

The test compound stock solution was diluted with an organic solvent (usually a mixture of acetonitrile, methanol and water with various ratios, depending on the solubility of the compound, if necessary, 1 N hydrochloric acid or 1 N sodium hydroxide would be added to facilitate solubilization) to the 0.1 mM (the final concentration of the compound in the reaction system was 1 µM) and the concentration percentage of the organic solvents in the incubation system no more than 1% (wherein the percentage of DMSO was required to be no more than 0.1%). An appropriate amount of 100 mM NADP, 500 mM G-6-P and 100 Unit/mL G-6-PDH were mixed and diluted with ultrapure water (the final system contains 1 mM NADP, 5 mM G-6-P and 1 Unit/mL G-6-PDH), pre-incubated in a 37° C. water bath for 10 minutes and then placed on ice for use as a NADPH regeneration solution. 20 mg/mL liver microsomes solution and 200 mM phosphate buffer were mixed, and diluted with ultrapure water to give a liver microsomes solution containing 2.5 mg/mL liver microsomes (the final concentration of the reaction system is 0.5 mg/mL) and 50 mM phosphate buffer. The diluted liver microsomes solution was mixed with 0.1 mM compound solution, a mixture of 100 mM EDTA, 300 mM $MgCl_2$ solution, 200 mM phosphate buffer (the final system was 3 mM $MgCl_2$, 1 mM EDTA and 50 mM phosphate buffer) and water in an appropriate volume was added. Finally, the NADPH regeneration solution was added, then the reaction solution was placed in a 37° C. water bath to start the reaction (the reaction time was 30 minutes), and the reaction was stopped by adding the ice-cold acetonitrile reaction stopping solution containing the internal standard. The 0-minute sample was not incubated in a 37° C. water bath, and its difference from the 30-minute sample further lies in that the ice-cold acetonitrile reaction stopping solution containing the internal standard was added first, and then the NADPH regeneration solution was added. The sample added with the reaction stopping internal standard solution was vortexed and mixed well, and then centrifuged at 4400 rpm for 10 minutes. The supernatant was taken and diluted ten times with 50% methanol for LC-MS/MS analysis.

4. Analysis Method:

LC-MS/MS was used to determine the concentration of the compound in the sample. The percentage of the remaining compound after 30 minutes of incubation comparing with that in the 0-minute sample was calculated using the peak area ratio of the compound to the internal standard as an indicator, to evaluate the metabolic stability of the compound.

Instrument: API4500, API4000 or LTQ Mass Spectrometer; the liquid phase is UHPLC system (Shimadzu LC-30 AD, model Nexra $X_2$) including liquid delivery unit, column thermostat, detector and autosampler; or Agilent 1200 Binary Pump series HPLC and CTC Autosampler.

Chromatographic column: Waters XSELECT Hss T3 $C_{18}$ (2.5 µm, 2.1×50 mm) or CAPCELLPAK MG (5 µm, 2.0×50 mm)

Mobile Phase:

A: water with 0.1% FA (formic acid) (with or without 0.1% ACN (acetonitrile))

B: acetonitrile with 0.1% FA (formic acid).

The test results are shown in the following table:

| Compound No. | RLM* | MLM** |
| --- | --- | --- |
| GDC-0853 | 81.0% | 76.3% |
| 1 | 87.9% | 91.6% |
| 2 | 85.7% | 92.6% |
| 4 | 97.4% | 90.9% |
| 5 | 95.4% | 67.5% |

*RLM, rat liver microsomes.
**MLM, mouse liver microsomes.

Example 6 Evaluation for In Vivo Efficacy of the Inhibitory Effect on BTK Target Objects: B cells in mice whole blood were induced and activated by the anti-IgD antibody, and the inhibitory effect of the compound of the present invention on B cell activation in vivo was studied, so as to determine the inhibitory effect of the compound of the present invention on the BTK target in vivo.

Methods: C57BL/6 mice (female, 18-20 g, purchased from Shanghai Lingchang Biotechnology Co., Ltd.) were grouped according to Table 1.

TABLE 1

Grouping information of in vivo administration

| Groups | Dose (mg/kg) | Number of animals | Vehicle | Dosing regimen | Administration volume | Time for blood collection after administration | Formulation |
|---|---|---|---|---|---|---|---|
| Vehicle group | 0 | 6 | 0.5% HPMC, pH = 3 | Oral gavage, single administration | 10 mL/kg in weight | 16 h | — |
| GDC-0853 | 20 | 3 | | | | 16 h | Solution |
| Compound 1 | 5 | 3 | | | | 16 h | Solution |
| Compound 2 | 20 | 3 | | | | 16 h | Solution |

The animals of each group were administered, then were placed in $CO_2$ for anesthesia at designated time points, blood samples were taken from rats via retro-orbital bleeding, and heparin was used for anticoagulation; 90 μL of whole blood was taken from mice of each group, and added to a 96 well culture plate, and anti-mouse IgD antibody (BIO-RAD, Cat #MCA4693) was added to each well to a final concentration of 0.01 μg/L (respectively for each drug-treated group and anti-IgD antibody-inducted vehicle group); in addition, 90 μL of whole blood of mice in the vehicle group was taken and added to the 96-well culture plate, and PBS (phosphate buffer, GIBCO, Cat #$C_{20012500}BT$) was added to each well to a final concentration of 0.01 μg/L (namely, the vehicle control group); Each group was mixed well and incubated in a 37° C./5% $CO_2$ incubator for 4 hours. In addition, the blood of mice in the drug-treated group was centrifuged to separate plasma for blood concentration analysis.

The cultured whole blood was added with fluorescently labeled antibodies Anti-CD19-APC (BD Biosciences, Cat #550992) and Anti-CD69-PE (BD Biosciences, Cat #553237), mixed well, and incubated at room temperature in the dark for 30 minutes; 50 L of the sample was transferred to a 96-well deep V-shaped culture plate containing 380 L of fresh lysis buffer (BD Biosciences, Cat #555899), shaken, and placed at room temperature in the dark for 15 minutes to remove red blood cells; 400 μL of flow buffer (2% FBS/PBS, FBS: fetal bovine serum, GIBCO, Cat #100100-147; PBS: GIBCO, Cat #C20012500BT) was added, centrifuged at 1200 rpm at 4° C. for 8 minutes; the supernatant was removed, the cell clumps were washed twice with FACS buffer, and centrifuged; then the cells were resuspended with 400 μL of FACS buffer, the expression of CD69+ in CD19+ positive cells (B cells) was detected using BD FACS LSR-Fortessa flow cytometer and the data was analyzed.

Calculation for B Cell Activation Ratio:

B cell activation ratio=percentage of $CD69^+CD19^+$ double positive B cells/percentage of $CD19^+$ single positive B cells Calculation for Inhibition Ratio:

Inhibition ratio=(percentage of B cell activation ratio in anti-IgD antibody-induced vehicle group-percentage of B cell activation ratio in drug-treated group)/(percentage of B cell activation ratio in anti-IgD antibody-induced vehicle group-percentage of B cell activation ratio in vehicle control group)×100%

All data are represented by mean±standard error. For the comparison between each drug-treated group and the anti-IgD antibody-induced vehicle group, p value was calculated by Graphpad Prism using one-way ANOVA analysis of variance and Dunnett's test, and for the comparison between each drug-treated group, p value was calculated by using unpaired t test.

Results: The experimental results are shown in FIG. 1 and Table 2.

In this experiment, after 16 hours of administration, the inhibition ratio of GDC-0853 20 mg/kg on B cell activation is 9%; and the inhibition ratio of compound 2 of the present invention at a dose of 20 mg/kg on B cell activation is 43%. The inhibition ratio of compound 1 of the present invention at a dose of 5 mg/kg on B cell activation is 60%, which has a statistically significant difference compared with the anti-IgD antibody-induced vehicle group.

TABLE 2

Effect of in vivo administration on anti-IgD antibody-induced B cell activation in mice whole blood

| Groups | Dose (mg/kg) | Time (h) | B cell activation ratio (the population of activated B cells in total B cells) | Inhibition ratio (%) | Drug concentration in plasma (ng/mL) |
|---|---|---|---|---|---|
| Vehicle control group | / | 16 | 5.6 ± 0.6 | 100% | / |
| Anti-IgD antibody-inducted vehicle group | / | 16 | 31.7 ± 2.2[####] | 0% | / |
| GDC-0853 | 20 | 16 | 29.3 ± 6.7 | 9% | 5.01 ± 2.26 |
| Compound 1 | 5 | 16 | 16.0 ± 3.9* | 60% | 6.27 ± 1.68 |
| Compound 2 | 20 | 16 | 20.6 ± 5.0 | 43% | 6.60 ± 2.51 |

[####]represents $p < 0.0001$ compared with the vehicle control group;
*represents $p < 0.05$ compared with the anti-IgD antibody-induced vehicle group.

Example 7 Therapeutic Effect of the Compound of the Present Invention on a Rat Arthritis Model Induced by Type II Collagen 1. Study Methods An appropriate amount of bovine type II collagen (CII, Chondrex (Redmond, WA, USA), Cat #20021) was weighed and dissolved in 0.1 mole of acetic acid (SPGC Sinopharm Chemical Reagent Co., Ltd (Shanghai, P.R. China), Cat #: 10000218.), which was formulated into a solution with a concentration of 6 mg/mL, stirred at 4° C. overnight, and added with an equal volume of Freund's incomplete adjuvant (Sigma-Aldrich. (St. Louis, MO, USA), Cat #: SLBW0366.), fully emulsified to prepare an emulsion with a CII concentration of 3 mg/mL.

Female Lewis rats were purchased from Beijing Vital River Laboratory Animal Technology Co., Ltd. (certificate number 20200928Aazz0619000579, initial body weight of 110-130 grams), and 6 rats were randomly selected as a normal group; and all of the remaining rats were immunized. In the first immunization on day 0, the rats except those in the normal group were anesthetized with isoflurane (Hebei Yipin Pharmaceutical Co., Ltd., Lot: C002170601.), and then disinfected with 75% alcohol, and 0.2 mL of emulsion was injected intradermally at the base of the tail thereof. A second challenge was carried out on day 7, and 0.2 mL of emulsion was intradermally injected using the same method. Once the animals developed symptoms on day 10, the incidence conditions thereof were closely monitored. Immunized animals had an average paw volume of 1.5-1.7 ml on day 13, and were randomly grouped and administered according to Table 3.

TABLE 3

Grouping information of modeling administration

| Groups | Modeling | Dose | Dosing regimen | Number of animals | Vehicle |
| --- | --- | --- | --- | --- | --- |
| Normal group | / | / | / | 6 rats | / |
| Vehicle control group | Day 0 and Day 7, 600 μg CII + IFA | 0 mg/kg | Once a day, from Day 13 (paw volume reaching 1.5 ml) to Day 19 | 8 rats in each group | 0.5% HPMC, pH 3 |
| GDC-0853-0.25 | | 0.25 mg/kg | | | |
| GDC-0853-4 | | 4 mg/kg | | | |
| Compound 1-0.06 | | 0.06 mg/kg | | | |
| Compound 1-0.25 | | 0.25 mg/kg | | | |
| Compound 1-4 | | 4 mg/kg | | | |

After grouping, the normal group was not administered, and the rats in the other groups were administered with the control vehicle, 0.25 mg/kg and 4 mg/kg of the reference GDC-0853, and each dose of compound 1 orally once a day until the end of the experiment. Grouping and dosage regimen are shown in Table 3.

The paw volume was measured on day 10 after immunization, and the left and right hind paw volumes (V) were measured every day after the paw volume increase was detected.

The arthrosis paw volumes of the left and right hind limbs of each animal were measured, and the average paw volume (APV) was calculated according to the following formula:

Average paw volume APV=$(V_{left}+V_{right})/2$

Effects of drugs on the average paw volume were subjected to statistical analysis by GraphPad with repeated measure ANOVA followed with Dunnett's multiple comparison test, and the p value was calculated, wherein ###$p<0.001$ indicated that there was a statistically extremely significant difference compared with the normal group, *$p<0.05$ indicated that there was a statistically significant difference compared with the vehicle control group, and **$p<0.01$ indicated that there was a statistically extremely significant difference compared with the vehicle control group. The average arthrosis paw volume of each animal before administration was used as the baseline (or considered 100% inhibition of inflammation). The averaged paw swelling (APS) of each animal is calculated according to the following formula, wherein, $APV_{d1}$ is the average paw volume of the animal administered on day 1, and $APV_{dt}$ is the average paw volume of the animal administered on day t:

The averaged paw swelling $APS_{dt}=(APV_{dt}-APV_{d1})$

The area under the curve (AUC) of the average paw volume swelling is the area under the curve of the arthrosis score swelling calculated by the trapezoid method, and the calculation formula is:

$$AUC_{APS}=1/2\times(APS_{d1}+APS_{d2})\times(d_2-d_1)+1/2\times(APS_{d2}+APS_{d3})\times(d_3-d_2)+\ldots+1/2\times(APS_{dn}+APS_{d(n-1)})\times(d_n-d_{n-1}).$$

The formula for calculating the inhibition ratio of area under the curve (IRAUC) is as follows:

Inhibition ratio $IR_{AUC}\%$=(Mean $AUC_{APS}$ in the model group-$AUC_{APS}$ in the drug-treated group)/(Mean $AUC_{APS}$ in the model group-Mean $AUC_{APS}$ in the normal group)×100%.

$ED_{50}$ is calculated by XLfit software according to the AUC inhibition ratio of the area under the curve of the average paw volume swelling. The selected model is "log (inhibitor) vs. response—Variable slope":

$$y = A + \frac{B-A}{1+\left(\frac{C}{x}\right)^D}.$$

2. Results

Figure 2:
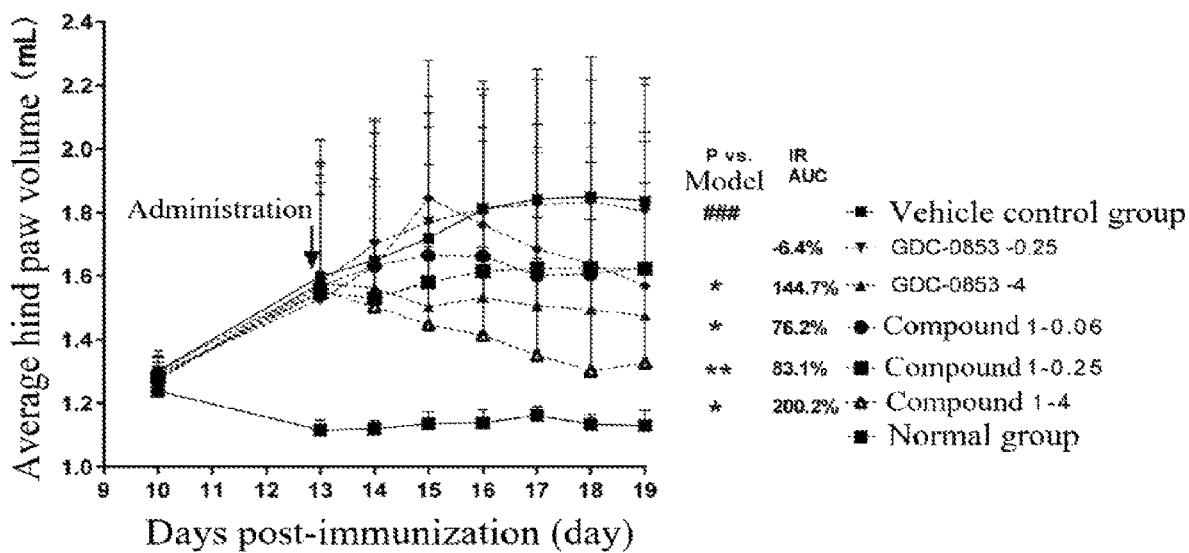
FIG. 2: Effects of the compounds of the present invention on the arthrosis paw volume in CIA (collagen induced arthritis) rats (the hind paw volume was measured by a Paw Volume Meter; the data were represented by mean±standard deviation; and each group respectively represented a normal group, a vehicle control group, 0.25 mg/kg and 4 mg/kg GDC-0853 groups, and compound 1 QD groups in different doses (normal group: n=6; other groups: n=8)).

Lewis rats started to show disease symptoms on day 10 after the first immunization with bovine type II collagen, and the paw volume of the hind limb gradually increased with the disease progression. The paw volume increase of the rat in the vehicle control group was compared with that in the normal group, and there was a statistically significant difference (###$p<0.001$). GDC-0853-0.25 mg/kg had no improvement effect on the increase of the paw volume of rats, and the paw volume of the rats administrated with GDC-0853-4 mg/kg was significantly reduced ($p<0.05$) compared with that in the vehicle control group. Oral administration of 0.06, 0.25 and 4 mg/kg QD of compound 1 solution once a day dose-dependently inhibited paw swelling, with the inhibition ratio of area under the curve ($IR_{AUC}$) of 76.2%, 83.1% and 200.2%, respectively; and the minimum effective dose was 0.06 mg/kg/day. There was a statistical difference between 0.25 mg/kg of compound 1 (inhibition ratio of area under the curve was 83.1%) and the same dose of GDC-0853 (inhibition ratio of area under the curve was −6.4%), and between 4 mg/kg of compound 1 (inhibition ratio of area under the curve was 200.2%) and the same dose of GDC-0853 (inhibition ratio of area under the curve was 144.7%). Both 0.25 mg/kg of compound 1 and 4 mg/kg of compound 1 can significantly increase the continuous improvement of paw volume swelling ($p<0.01$, one-way repeated measure ANOVA, test by Graphpad). The results are as shown in FIG. 2.

Example 8 Therapeutic Effect of the Compounds of the Present Invention on Idiopathic Thrombocytopenic Purpura Induced by Anti-CD41 Antibody 1. Study Methods Male C57BL/6 mice were purchased from Shanghai Lingchang Biotechnology Co., Ltd. (certificate number 20180003011079, initial body weight of 18-20 grams), and were randomly grouped according to Table 4, with 8 mice in each group. Before modeling as shown in Table 4, mice were respectively administered in a single dose at different times: intraperitoneal injection of 2000 mg/kg of positive drug IVIg (Rongsheng, Lot #: 201604B026), oral administration of 40 mg/kg ofPRN1008 (rilzabrutinib) and different doses of compound 1. When modeling, each mouse was intraperitoneally injected with 200 μL of PBS solution containing 2 μg of anti-mouse CD41 antibodies (BD, Cat #: 553487, Lot #: 7026765).

TABLE 4

Grouping information of modeling administration

| Groups | Modeling | Dose (mg/kg) | Number of animals | Dosing regimen | Vehicle |
|---|---|---|---|---|---|
| Normal group | 200 uL PBS, i.p., | — | 8 | — | 0.5% HPMC, pH 3 |
| Vehicle control group | 200 μL of PBS solution containing 2 μg of anti-mouse CD41 antibodies, i.p., | — | 8 | Orally administration of a single dose, 2 hours before modeling | |
| PRN1008 | | 40 | 8 | Orally administration of a single dose, 1 hour before modeling | |
| Compound 1 | | 0.004 0.04 0.4 4 | 8 8 8 8 | Orally administration of a single dose, 18 minutes before modeling | |
| IVIg | | 2000 | 8 | Intraperitoneal injection of a single dose, 24 hours before modeling | |

Eight hours and twenty-four hours after modeling, the whole blood was collected and placed in a centrifuge tube coated with 10% citrate-phosphate-dextrose-adenine (CPDA), and the level of platelets (PLT) in the whole blood was measured by an XT-2000i (SYSMEX) automatic blood analyzer (Shanghai Laboratory Animal Research Centre Sino-British SIPPR/B & K Lab Animal Ltd).

The average level of platelets in peripheral blood was analyzed with Graphpad statistical software by one way ANOVA followed by Fisher LSD multiple comparison test, and the p value was calculated, wherein *$p<0.05$ indicated a statistically significant difference compared with the vehicle control group, **$p<0.01$ indicated a statistically extremely significant difference compared with the vehicle control group, and ##$p<0.01$ indicated a statistically extremely significant difference compared with the normal group.

The recovery rate (RR) of the level of platelets is calculated according to the following formula:

$$RR\% = (PLT_{treatment} - PLT_{model})/(PLT_{naive} - PLT_{model}) \times 100\%.$$

2. Results

Eight hours after intraperitoneal injection of anti-mouse CD41 antibodies, the level of platelets in peripheral blood of C57BL/6 mice was measured. There was a statistically extremely significant difference of average level of platelets in the vehicle control group compared with that in the normal group (##$p<0.01$). Compared with the vehicle control group, intraperitoneal injection of 2 g/kg of IVIg showed a significant recovery in the level of platelets ($p<0.01$), with the recovery rate of platelets of 54%. Compared with the vehicle control group, oral administration of 40 mg/kg of PRN1008 showed a significant recovery in the level of platelets ($p<0.01$), with the recovery rate of platelets of 40%. A single oral administration of 0.004, 0.04, 0.4 and 4 mg/kg of compound 1 solution dose-dependently restored the reduction in platelets induced by anti-mouse CD41 antibodies, with the recovery rate of platelets of 25%, 37%, 44% and 51%, respectively; and the minimum effective dose was 0.04 mg/kg.

Figure 3:
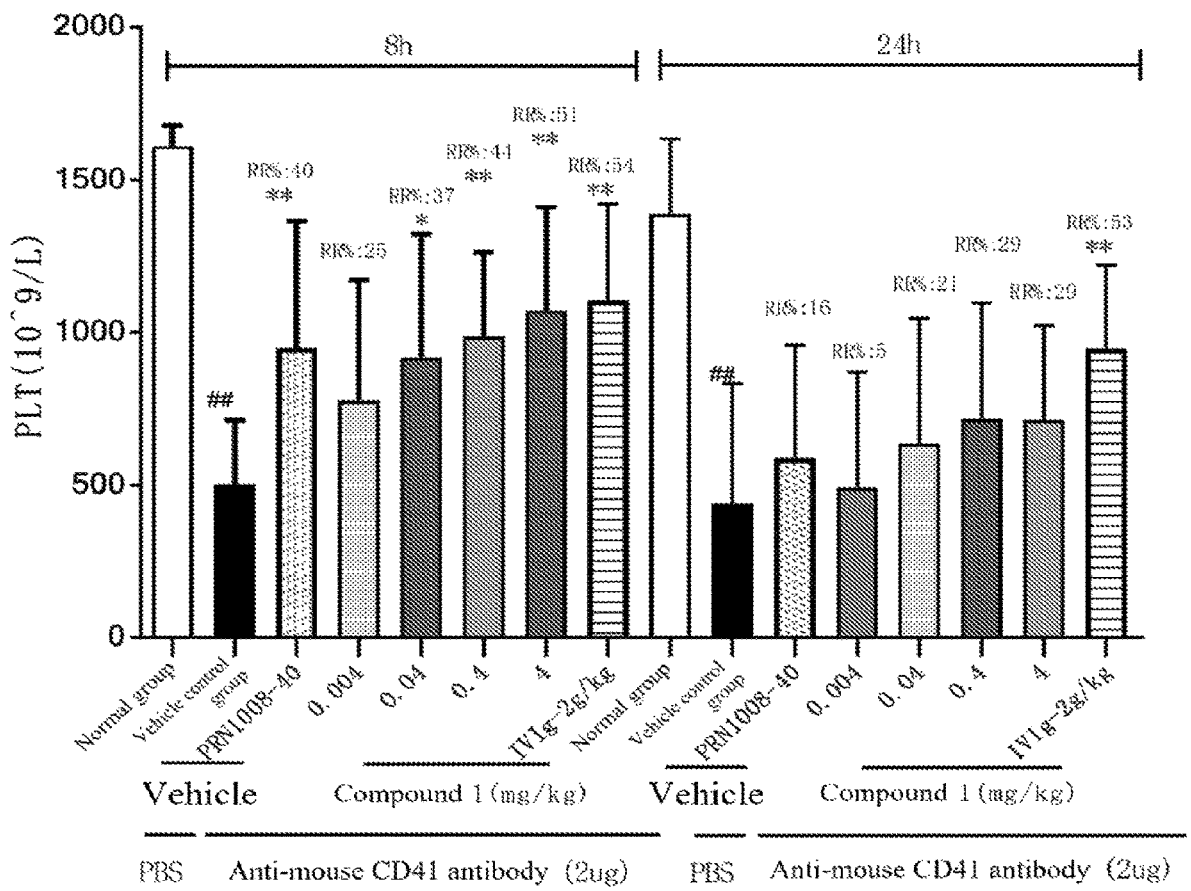
FIG. 3: Effects of the compounds of the present invention on the level of platelets in peripheral blood of ITP (idiopathic thrombocytopenic purpura induced by anti-mouse CD41 antibodies) mice. The level of platelets was measured by an automatic blood analyzer; the data were represented by mean±standard deviation; and each group respectively represented a normal group and modeling groups (i.e., a vehicle control group, a 40 mg/kg PRN1008 group and compound 1 groups in different doses, respectively) (each group: N=8).

Twenty-four hours after intraperitoneal injection of anti-mouse CD41 antibodies, the level of platelets in peripheral blood of C57BL/6 mice was measured. There was a statistically extremely significant difference of average level of platelets in the vehicle control group compared with that in the normal group (##, $p<0.01$). Compared with the vehicle control group, intraperitoneal injection of 2 g/kg of IVIg showed a significant recovery in the level of platelets (**$p<0.01$), with the recovery rate of platelets of 53%. Compared with the vehicle control group, oral administration of 40 mg/kg of PRN1008 showed no significant recovery in the average level of platelets, with the recovery rate of platelets of only 16%. A single oral administration of 0.004, 0.04, 0.4 and 4 mg/kg of compound 1 solution dose-dependently restored the reduction in platelets induced by anti-mouse CD41 antibodies, with the recovery rate of platelets of 5%, 21%, 29% and 29%, respectively. The results are as shown in FIG. 3.

The invention claimed is:

1. A compound of formula (I):

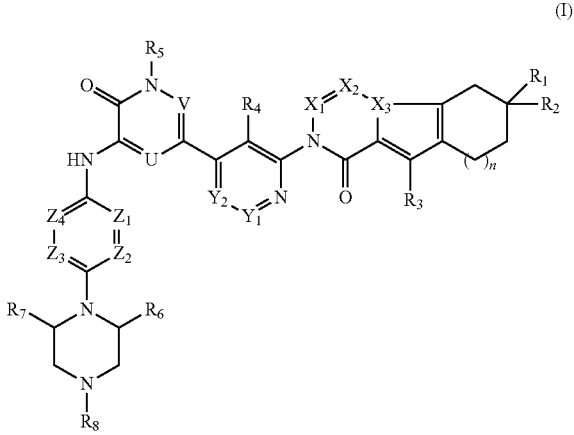

(I)

or a pharmaceutically acceptable salt, stereoisomer, or tautomer thereof, wherein:
X₁ is CH or N;
X₂ is CH or N;
X₃ is CH or N;
R₁ is H, D, halogen, CN, $C_{1-6}$ alkyl, $C_{1-6}$ deuteroalkyl, $C_{1-6}$ haloalkyl, $C_{2-6}$ alkynyl, OH, or $C_{3-6}$ cycloalkyl;
R₂ is H, D, halogen, CN, $C_{1-6}$ alkyl, $C_{1-6}$ deuteroalkyl, $C_{1-6}$ haloalkyl, $C_{2-6}$ alkynyl, OH, or $C_{3-6}$ cycloalkyl; or
R₁ and R₂, together with the carbon atom to which they are attached, form a $C_{3-6}$ cycloalkyl;
R₃ is H, D, halogen, CN, or $C_{1-6}$ haloalkyl;
R₄ is H, halogen, CN, $C_{1-6}$ alkyl, $C_{1-3}$ alkyl-OH, $C_{1-3}$ alkyl-O$C_{1-3}$ alkyl, $C_{2-6}$ alkynyl, C(O)H, C(O)NH₂, C(O)NHCH₃, C(O)N(CH₃)₂, O$C_{1-3}$ alkyl, or 3-hydroxyoxetan-3-yl, wherein the $C_{1-6}$ alkyl and each $C_{1-3}$ alkyl of the $C_{1-3}$ alkyl-OH, $C_{1-3}$ alkyl-O$C_{1-3}$ alkyl, or O$C_{1-3}$ alkyl is optionally substituted with one or more substituents independently selected from the group consisting of D and halogen;
Y₁ is CR₁₀;
Y₂ is CR₁₀;
each R₁₀ is independently H, D, halogen, CN, $C_{1-6}$ alkyl, or $C_{1-6}$ haloalkyl;
R₅ is H, $C_{1-6}$ alkyl, or $C_{3-6}$ cycloalkyl, wherein the $C_{1-6}$ alkyl is optionally substituted with one or more substituents independently selected from the group consisting of D and halogen;
U is CR₉;
V is CR₉;
each R₉ is independently H, D, or halogen;
Z₁ is N;
Z₂ is CH;
Z₃ is CH;
Z₄ is CH;
R₆ is $C_{1-6}$ alkyl;
R₇ is $C_{1-6}$ alkyl;
R₈ is H, $C_{1-6}$ alkyl, $C_{3-6}$ cycloalkyl, or 4- to 8-membered heterocyclyl, wherein the $C_{1-6}$ alkyl, $C_{3-6}$ cycloalkyl, or 4- to 8-membered heterocyclyl is optionally substituted with one or more substituents independently selected from the group consisting of D, halogen, $C_{1-6}$ alkyl, CF₃, NH₂, NHC$_{1-6}$ alkyl, N(C$_{1-6}$ alkyl)₂, OH, and OC$_{1-6}$ alkyl; and
n is 0, 1, or 2;
with the proviso that if n is 1, then R₃ is not H.

2. The compound according to claim 1, or a pharmaceutically acceptable salt, stereoisomer, or tautomer thereof, wherein:
R₁ is H, D, halogen, CN, $C_{1-6}$ alkyl, $C_{1-6}$ deuteroalkyl, $C_{1-6}$ haloalkyl, or OH;
R₂ is H, D, halogen, CN, $C_{1-6}$ alkyl, $C_{1-6}$ deuteroalkyl, $C_{1-6}$ haloalkyl, or OH;
R₄ is $C_{1-3}$ alkyl-OH, C(O)NH₂, C(O)NHCH₃, or C(O)N(CH₃)₂, wherein the $C_{1-3}$ alkyl of the $C_{1-3}$ alkyl-OH is optionally substituted with one or more D substituents;
Y₁ is CR₁₀;
Y₂ is CR₁₀;
each R₁₀ is independently H or D;
R₅ is H or $C_{1-6}$ alkyl, wherein the $C_{1-6}$ alkyl is optionally substituted with one or more D substituents;
U is CR₉;
V is CR₉;
each R₉ is independently H or D; and
R₈ is H, $C_{1-6}$ alkyl, $C_{3-6}$ cycloalkyl, or 4- to 8-membered heterocyclyl, wherein the $C_{1-6}$ alkyl, $C_{3-6}$ cycloalkyl, or 4- to 8-membered heterocyclyl is optionally substituted with one or more substituents independently selected from the group consisting of D, halogen, $C_{1-6}$ alkyl, CF₃, NH₂, and OH.

3. The compound according to claim 2, or a pharmaceutically acceptable salt, stereoisomer, or tautomer thereof, wherein:
X₁ is CH; and
X₂ is CH.

4. The compound according to claim 2, or a pharmaceutically acceptable salt, stereoisomer, or tautomer thereof, wherein X₃ is N.

5. The compound according to claim 2, or a pharmaceutically acceptable salt, stereoisomer, or tautomer thereof, wherein:
R₁ is $C_{1-6}$ alkyl; and
R₂ is $C_{1-6}$ alkyl.

6. The compound according to claim 2, or a pharmaceutically acceptable salt, stereoisomer, or tautomer thereof, wherein R₃ is H or halogen.

7. The compound according to claim 2, or a pharmaceutically acceptable salt, stereoisomer, or tautomer thereof, wherein R₄ is $C_{1-3}$ alkyl-OH or $C_{1-3}$ deuteroalkyl-OH.

8. The compound according to claim 2, or a pharmaceutically acceptable salt, stereoisomer, or tautomer thereof, wherein:
R₃ is H; and
$R_a$ is $C_{1-3}$ alkyl-OH.

9. The compound according to claim 2, or a pharmaceutically acceptable salt, stereoisomer, or tautomer thereof, wherein each R₁₀ is independently H.

10. The compound according to claim 2, or a pharmaceutically acceptable salt, stereoisomer, or tautomer thereof, wherein R₅ is $C_{1-6}$ alkyl.

11. The compound according to claim 2, or a pharmaceutically acceptable salt, stereoisomer, or tautomer thereof, wherein:
U is CH; and
V is CH.

12. The compound according to claim 2, or a pharmaceutically acceptable salt, stereoisomer, or tautomer thereof, wherein:
R₆ is CH₃; and
R₇ is CH₃.

13. The compound according to claim 2, or a pharmaceutically acceptable salt, stereoisomer, or tautomer thereof, wherein R₈ is oxetanyl or tetrahydrofuranyl.

14. The compound according to claim 13, or a pharmaceutically acceptable salt, stereoisomer, or tautomer thereof, wherein R₈ is oxetan-3-yl.

15. The compound according to claim 2, or a stereoisomer thereof, wherein the compound, or stereoisomer thereof, is selected from the group consisting of:

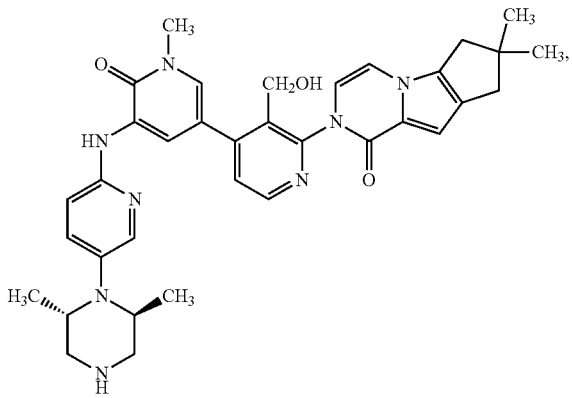

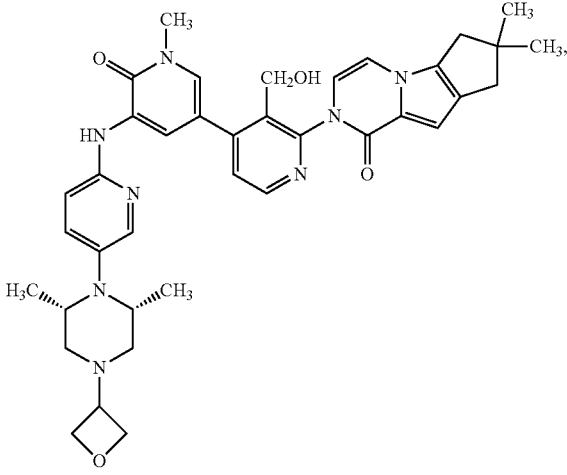

and

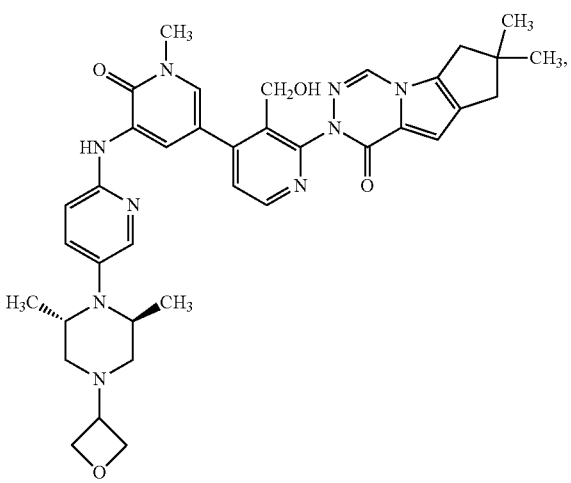

or a pharmaceutically acceptable salt thereof.

16. A pharmaceutical composition comprising a pharmaceutically acceptable excipient and the compound according to claim 2, or a pharmaceutically acceptable salt, stereoisomer, or tautomer thereof.

17. A pharmaceutical combination comprising the compound according to claim 2, or a pharmaceutically acceptable salt, stereoisomer, or tautomer thereof, and at least one additional therapeutic agent.

18. The pharmaceutical combination according to claim 17, wherein the additional therapeutic agent is selected from the group consisting of an anti-inflammatory agent, an anti-tumor active agent, and an immunomodulator.

19. The pharmaceutical combination according to claim 18, wherein the anti-tumor active agent is selected from the group consisting of a chemotherapeutic agent, an immune checkpoint agonist, an immune checkpoint inhibitor, and a targeted therapeutic agent.

20. A method for inhibiting Bruton's tyrosine kinase (BTK) activity in a cell, wherein the method comprises contacting the cell with an effective amount of the compound according to claim 2, or a pharmaceutically acceptable salt, stereoisomer, or tautomer thereof.

21. A method for inhibiting Bruton's tyrosine kinase (BTK) activity in a subject, wherein the method comprises administering to the subject in need thereof a therapeutically effective amount of the compound according to claim 2, or a pharmaceutically acceptable salt, stereoisomer, or tautomer thereof.

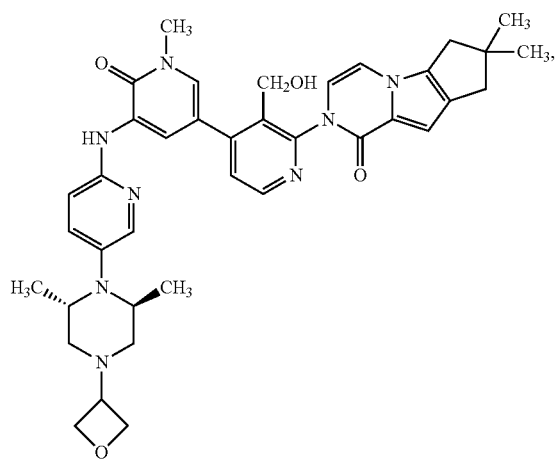

22. The method according to claim 21, wherein the subject has a disease mediated at least in part by Bruton's tyrosine kinase (BTK) selected from the group consisting of an autoimmune disease, cancer, graft versus host disease, and an inflammatory disease.

23. The method according to claim 22, wherein the autoimmune disease, graft versus host disease, or inflammatory disease is selected from the group consisting of acute idiopathic polyneuritis, allergic disease, antineutrophil cytoplasmic antibody vasculitis, arthritis, asthma, autoimmune hemolytic anemia, autoimmune thyroid disease, chronic lymphocytic thyroiditis, chronic obstructive pulmonary disease, Crohn's disease, dermatitis, goodpasture syndrome, hyperthyroidism, idiopathic thrombocytopenic purpura, inflammation associated with immunosuppression, local inflammation, lupus erythematosus, mixed connective tissue disease, multiple sclerosis, organ-graft rejection, osteoporosis, pemphigoid, pemphigus vulgaris, pernicious anemia with chronic atrophic gastritis, primary biliary cirrhosis, psoriasis, scleroderma, sicca syndrome, Sjögren syndrome, systemic inflammation, ulcerative colitis, and a disease associated with kidney transplantation.

24. The method according to claim 23, wherein the arthritis is rheumatoid arthritis.

25. The method according to claim 23, wherein the lupus erythematosus is systemic lupus erythematosus.

26. The method according to claim 22, wherein the cancer is a solid tumor or a hematologic malignancy.

27. The method according to claim 26, wherein the solid tumor or hematologic malignancy is selected from the group consisting of leukemia, lymphoma, and myeloma.

28. The method according to claim 22, wherein the cancer is selected from the group consisting of acute lymphoblastic leukemia, B-cell lymphoma, B-cell malignancy, Burkitt's lymphoma, follicular lymphoma, hairy cell leukemia, Hodgkin's lymphoma, human acute monocytic leukemia, lymphoblastic lymphoma, lymphocytic leukemia, mantle cell lymphoma, marginal zone lymphoma, myelodysplastic syndrome, myelogenous leukemia, myeloma, non-Hodgkin's lymphoma, small lymphocytic lymphoma (SLL), and Waldenstrom's macroglobulinemia.

29. The method according to claim 28, wherein the B-cell lymphoma is selected from the group consisting of extranodal marginal-zone B-cell lymphoma, highly aggressive non-Burkitt's B cell lymphoma, and large B-cell lymphoma (LBCL).

30. The method according to claim 29, wherein the large B-cell lymphoma is diffuse large B-cell lymphoma (DLBCL).

31. The method according to claim 28, wherein the lymphocytic leukemia is selected from the group consisting of acute lymphocytic leukemia (ALL) or chronic lymphocytic leukemia (CLL).

32. The method according to claim 31, wherein the acute lymphocytic leukemia (ALL) or chronic lymphocytic leukemia (CLL) is B cell acute lymphocytic leukemia (B-ALL) or high risk chronic lymphocytic leukemia (high risk CLL).

33. The method according to claim 28, wherein the myelogenous leukemia is acute myelogenous leukemia (AML) or chronic myelogenous leukemia (CML).

34. The method according to claim 28, wherein the myeloma is multiple myeloma.

* * * * *